(12) United States Patent
Lomans et al.

(10) Patent No.: US 8,349,819 B2
(45) Date of Patent: *Jan. 8, 2013

(54) STEROID EXTRACTION PROCESS FROM URINE SOURCES

(75) Inventors: John Lomans, Middleburgh, NY (US); Carmen Leiva-paredes, Schoharie, NY (US)

(73) Assignee: Dr. Reddy's Laboratories New York, Inc., Bridgewater, NJ (US)

( * ) Notice: Subject to any disclaimer, the term of this patent is extended or adjusted under 35 U.S.C. 154(b) by 785 days.

This patent is subject to a terminal disclaimer.

(21) Appl. No.: 11/055,257

(22) Filed: Feb. 10, 2005

(65) Prior Publication Data
US 2005/0164998 A1 Jul. 28, 2005

Related U.S. Application Data

(63) Continuation-in-part of application No. 10/266,754, filed on Oct. 9, 2002, now Pat. No. 6,855,704.

(51) Int. Cl.
*A01N 45/00* (2006.01)
*A61K 31/56* (2006.01)
*A61K 35/22* (2006.01)
*C07J 3/00* (2006.01)

(52) U.S. Cl. ......... 514/170; 424/545; 552/503; 552/625

(58) Field of Classification Search .................. 514/170; 424/545; 552/503, 625
See application file for complete search history.

(56) References Cited

U.S. PATENT DOCUMENTS

| | | | |
|---|---|---|---|
| 2,551,205 A | 5/1951 | Cook et al. | |
| 2,696,265 A | 12/1954 | Beall et al. | |
| 2,711,988 A | 6/1955 | Deans et al. | |
| 2,834,712 A | 5/1958 | Beall et al. | |
| 3,769,401 A | 10/1973 | Thompson | |
| 4,154,820 A * | 5/1979 | Simoons | 514/178 |
| 5,210,081 A | 5/1993 | Raveendranath et al. | |
| 5,616,407 A * | 4/1997 | Fritz et al. | 442/118 |
| 5,723,454 A * | 3/1998 | Ban et al. | 514/169 |
| 5,814,624 A * | 9/1998 | Ban et al. | 514/170 |
| 5,908,638 A | 6/1999 | Huber et al. | |
| 6,855,704 B2 | 2/2005 | Lomans et al. | |
| 7,081,451 B2 * | 7/2006 | Ahnsorge et al. | 514/170 |
| 2001/0034340 A1 | 10/2001 | Pickar | |
| 2002/0156303 A1 | 10/2002 | Soong et al. | |
| 2003/0105344 A1 * | 6/2003 | Ahnsorge et al. | 552/625 |
| 2003/0215953 A1 | 11/2003 | Rasche et al. | |
| 2004/0072812 A1 | 4/2004 | Lomans et al. | |

FOREIGN PATENT DOCUMENTS

| | | |
|---|---|---|
| WO | 01/27134 | 4/2001 |
| WO | 03/048183 | 6/2003 |
| WO | 03/051337 | 6/2003 |

OTHER PUBLICATIONS

Pasto et al. (Experiments and Techniques in Organic Chemistry, Chapter 2: the Separation and Purification Technique, Section: 2.6-2.6.2: Chromatography & Adsorption Chromatography, 1992 Edition).*
Merck Index 13th Edition (2001), Entry 2533.
Stedman's Medical Dictionary, 26th Edition, (1995) p. 600-601.
PDR Medical Dictionary 2nd Edition, (2000) p. 621-622.
USP 27 (2004) p. 747-750.
Itochn product Literature on resins.
FDA Guidance for Industry Conjugated , USP—LC, MS Method for Quatitative Characterization and Documentation of Qualitative Pharmaceutical Equivalence Mar. 2000.
Bradlow, Steroids 11:265-272, 1968.
Okerholm et al, Quantitative Extraction of Steroid Conjugates from Urine by Use of a Liquid-Liquid Partition System; Steroids 16:1 65-68, Jul. 1970.
Arcos et al; Extraction of Steroid Conjugates from Urine Using Charcoal as an Adsorbent; J. Clin. Endocrinology and metabolism 25, 808-816 (Jul. 1965).
Smith et al; The Estrogens of Urine from Women: Hydrolysis, Separation and Extraction; Endocrinology 25, 509-519, 1939.
Schachter; The Isolation of Estrone Sulfate from the Urine of Pregnant Mares; Journal of Biological Chemistry (1938) 126, 663-666.
Koole; Solid Phae extraction for Multi-Residue Analysis of Anabolic Steroids and Related Substances from Calf Urine Using C18 and Alumina Columns; J. Liq. chrom. & Rel. Technol. 22 (17), 2627-2650 (1999).

(Continued)

*Primary Examiner* — Mina Haghighatian
*Assistant Examiner* — Helen Chui
(74) *Attorney, Agent, or Firm* — Gilman Pergament LLP

(57) ABSTRACT

A process in which urine is optionally filtered to remove solid extraneous matter and optionally treated so as to reduce the phenolic content of the urine to give and the resulting fluid is then subjected to a solid extraction of the major concentration steroids content therefrom by a first suitable resin (to yield a first resin laden with major concentration steroids and a minor concentration steroid laden first liquid remainder). The minor concentration steroid liquid remainder is subjected to a solid extraction of the minor concentration steroid content therefrom by a second suitable resin (to yield a second resin laden with minor concentration steroids and a second liquid remainder). The first and second resins laden with their respective steroids are then eluted and the eluates are collected separately and optionally subjected to further purification and chromatographic separations, with each resulting separate collection being analyzed for the steroid content thereof. The separate analyzed materials are dried and stored for recombination in an appropriate manner to meet a desired profile. The ultimate product has very nearly the same steroid components and concentrations from batch to batch.

27 Claims, 11 Drawing Sheets

OTHER PUBLICATIONS

Isobe et al; Determination of estrogens and their conjugates in water using solid-phase extraction followed by liquid chrmatography-tandem mass spectrometry; Journal of Chromatography A, 984(2003) 195-202.

Klyne et al; The Steroids of Pregnant mare's Urine; Biochemical Journal 43, 231-234 (1948).

Kammer et al: Extraction of Steroid Conjugates from Aqueous Solutions; Analytical Biochemistry 28, 492-502 (1969).

Muslim et al; Extraction of Oestrogen conjugates from Urine; Journal of Steroid Biochemistry 1970, vol. 1, 261-263.

Hahnel; The Separation of Oestrogen Conjugates from Human Urine; Clin. Chim. Acta, 7 ( 1962) 768-775.

Plager; Extraction and Purification of Steroid Conjugates with Ion Exchange Resins: measurement of Androsterone Sulfate and Debydroeplandrosterone Sulfate In Plasma; J Clin Endocr 26:1275 (1966).

* cited by examiner

STEROID EXTRACTION PROCESS FROM URINE SOURCES

CROSS-REFERENCE TO RELATED APPLICATIONS

This application is a continuation-in-part of U.S. patent application Ser. No. 10/266,754, filed Oct. 9, 2002 now U.S. Pat. No. 6,855,704.

STATEMENT REGARDING FEDERALLY SPONSORED RESEARCH OR DEVELOPMENT

Not Applicable

FIELD OF THE INVENTION

The present invention relates to extraction of steroids from urine sources. The invention also relates to the use of resins as extraction agents to remove either contaminants or various undesired steroids. The invention also relates to the various steroids that can be isolated from urine and to products that can be made from such isolates. In a preferred embodiment, the invention particularly relates to isolation and use of estrogens from female mammalian urine, in particular, mare's urine, especially pregnant mare's urine. The invention further relates to the use of particular resins in the extraction process and the order in which those resins are employed. The invention further relates to obtaining a defined, reproducible product containing conjugated estrogens which has substantially less variability in content from batch to batch than the prior art. Still further, the invention relates to the use of the steroids isolated to prepare therapeutic formulations and the use thereof in the treatment of medical conditions that are treatable with such steroids.

BACKGROUND OF THE INVENTION

All mammals produce steroids which are cleared from the body in varying degrees and excreted through the urine. Different species produce certain chemically unique steroids, while most species produce a number of steroids in common. Most mammalian species produce different relative levels of different steroids at various times during the day, season, and life cycle. Each of these may be excreted in varying degrees and potentially each is recoverable from the urine of such mammal. Steroid content of urine also differs significantly between males and females, between immature and mature members of the species and aged members of the species. Differences also appear between females capable of producing offspring who are pregnant, not pregnant but in estrus, as well as those who are not pregnant and not in estrus.

During the normal life cycle, a woman naturally reaches a point in time where her menstrual cycle stops. This is the basic definition of menopause and is typically characterized by the cessation of ovarian function, leading to a substantial reduction in circulating estrogens. Following the cessation of menses, the decline in endogenous estrogens is typically rapid from 40-250 pg/ml of estradiol and 40-170 pg/ml of estrone during ovulatory cycles to less than 15 pg/ml of estradiol and 30 pg/ml of estrone in postmenopausal women.

Physiologic changes that may result as a women moves from normal menstrual cycles and estrogen levels to an intermediate stage (perimenopause) through menopause to a postmenopausal condition include vulvar and vaginal atrophy causing vaginal dryness, pruritis and dysparenuria, and vasomotor instability manifested by hot flushes. Other menopausal disturbances may include depression, insomnia, and nervousness. Long-term effects of postmenopausal estrogen deprivation may result in significant morbidity and mortality due to the increase in risk factors for cardiovascular disease and osteoporosis. Menopausal changes in blood lipid levels may be precursors to increased incidence of ischemic heart disease and atherosclerosis, and other cardiovascular disease.

Estrogen replacement therapy (ERT) has provided beneficial symptomatic relief for the hot flushes, genital atrophy, symptoms and for the prevention of postmenopausal osteoporosis. In addition, ERT has been shown to be effective in increasing high-density lipoprotein-cholesterol and in reducing low-density lipoprotein-cholesterol giving some protection against cardiovascular heart disease, as well as other beneficial effects. The best known oral ERT available in the United States is a natural mixture of conjugated equine estrogens available under the name PREMARIN®. The Merck Index $13^{th}$ Edition (2001) defines "conjugated estrogenic hormones" (entry 2533) as "an amorphous preparation containing water-soluble, conjugated forms of mixed estrogens obtained from urine of pregnant mares" and that the principal estrogen present is sodium estrone sulfate. Both Stedman's Medical Dictionary, $26^{th}$ Edition, p. 600 (1995) and PDR Medical Dictionary, $2^{nd}$ Ed. p. 622 (2000) define conjugated estrogens in the same manner. The latter two references also define "esterified estrogens" as mixtures of sodium salts of sulfate esters of estrogenic substances. The USP 27 (2004) defines "conjugated estrogens" as a mixture of sodium estrone sulfate and sodium equiline sulfate, derived wholly or in part from equine urine or synthetically from estrone or equiline and contains other conjugated estrogenic substances of the type excreted by pregnant mares. The USP 27 defines "esterified estrogens" as a mixture of the sodium salts of sulfate esters of the estrogenic substances, principally estrone.

For purposes of clarity, the following definitions will be used in the present specification:

1) "esterified steroid" shall mean a steroid that has one or more groups esterified;
2) "sulfated steroid" shall mean a steroid that has one or more sulfate groups esterifying the steroid;
3) "sodium sulfated steroid" shall mean the sodium salt of the sulfate ester of the steroid;
4) "esterified estrogen" shall have the meaning given in the USP 27 set forth above;
5) "conjugated estrogens" shall have the meaning given in the USP 27 set forth above.

Unless the specific context of the text requires otherwise, the use of the term "salt" in conjunction with either of 1) or 2) above shall mean a salt selected from the group consisting of alkali metal salts, alkaline earth metal salts, and ammonium salts, with particular preference for the alkali metal salts, and special preference for the sodium salt.

Unfortunately, elevated estrogen levels have been related with an increased risk of endometrial cancer. Thus, the minimal dose of estrogens to achieve the desired result is essential to adequately balance the risks and benefits of estrogen therapy. The addition of progestin to therapy also lessens the endometrial cancer risk and for many women combination hormone replacement therapy (HRT) is a rational approach.

As noted, natural mixtures of conjugated estrogens (such as are found in the urine of pregnant mares) have proven particularly effective and well tolerated for ERT and HRT. The dissolved solids content in the urine of pregnant mares (PMU) may naturally vary within wide ranges, and generally lie in a range of about 40-90 g of dry matter per liter of urine. In addition to urea and other usual urine contents PMU generally contains about 2 to about 5% (of the dry matter—i.e. about 0.8 g/l to about 4.5 g/l) of phenolic constituents, which include cresols and dihydro-3,4-bis[(3-hydroxyphenyl)methyl]-2(3H)-furanone (HPMF), which may be present in free form or as salts of the sulfate esters thereof. Furthermore, the PMU has a natural mixture of estrogens that are largely present in conjugated form (i.e. as the sulfuric acid semi-ester sodium salt, also referred to as the "sulfate salt"). These sodium sulfated estrogens are typically present in an amount of about 0.3% to about 1% relative to the PMU dry matter (i.e., about 0.12 g/l to about 0.9 g/l of PMU).

In the early days of conjugated estrogen extraction from PMU, liquid-liquid extractions were employed using organic solvents that were immiscible or only slightly miscible with water, such as ethyl acetate, n-butanol, isobutanol, or cyclohexanol. However, such liquid-liquid extraction procedures resulted in problems such as severe foaming, sedimentation, emulsification, and poor phase separation, and several extraction steps were usually required. This led to processing losses and only partial recovery of the estrogen content of the PMU. Liquid-liquid extraction processes are disclosed in, for example, U.S. Pat. Nos. 2,551,205; 2,696,265; 2,711,988; 2,834,712 and WO01/27134 (corresponding to PCT/US99/23730) (all of which are incorporated herein in their entirety by reference).

Solid extractions using resins were first proposed by Bradlow (Steroids 11:265-272 (1968)) wherein a neutral, non-polar hydrophobic polystyrene resin, Amberlite XAD-2 (Rohm and Haas), was used. According to Bradlow, optionally diluted urine is passed through an Amberlite XAD-2 packed column using a low rate of flow, which absorbs the conjugated estrogens (although the absorption capacity is low), and the absorbed estrogens are eluted with methanol or ethanol. While this my have been suitable for an analytical process, the low rate of absorption did not make it practical as a commercial extraction process for obtaining large quantities of the steroids.

Other solid extractions of conjugated estrogens from PMU have been described in U.S. Pat. No. 3,769,401 (using a polyamine anion exchange resin (such as Dowex 1-X-2)); U.S. Pat. No. 5,723,454 (using a semi-polar porous, non-ionic adsorber resin (such as a cross-linked aliphatic polycarboxylic acid ester resin for example Amberlite XAD-7); U.S. Pat. No. 5,814,624 (using a hydrophobized silica gel a.k.a. a reverse-phase silica gel); US 2002/0156303 (using a polystyrene divinylbenzene resin); US 2003/0105344 (using a resin to extract all estrogenic components of the natural mixture in the PMU so that the volume to be transmitted to the laboratory from the field is reduced); and US 2003/0215953 using silicone membranes to separate the cresol components from the PMU before contacting the cresol reduced PMU with an adsorber resin; all of which are incorporated herein by reference. In each case, the adsorbed conjugated estrogens are eluted from the resin using a water-miscible organic solvent. Each of the foregoing US patents and applications is incorporated in its entirety herein by reference.

In addition to the processing issues themselves, the estrogenic content of PMU varies from batch to batch, even with respect to the currently marketed product PREMARIN. The total estrogen content varies as well as the presence or absence of some of the estrogenic components depending upon the mare, and what stage of pregnancy the mare is in when the urine is collected. Thus, the simple extraction of "estrogens" or of "conjugated estrogens" leads to a "conjugated estrogen product" that varies both in relative concentration (one steroid component relative to another steroid component) as well as in the presence of a number of the "estrogenic species" (some species may be missing from one batch and present in another). This has led to difficulties in development of a generic equivalent of PREMARIN, mostly because of the lack of a defined reference standard and the complex nature of the product.

Despite the advances in the extraction of estrogenic materials from urine, the processes can be improved upon in terms of yields, volumes of materials needed for processing the urine; and especially in consistency of product that results from the process. In addition, given the size of the market for conjugated estrogens, a source of a generic alternative has and continues to be desired.

In addition, during the extraction process for obtaining a particular set of steroids, many other steroids of commercial value are obtained and can be isolated with relatively small additional cost, or can be obtained as commercially valuable mixtures of different sets of steroids useful for human, veterinary, agricultural, and chemical purposes.

OBJECTS OF THE INVENTION

It is among the objects of the present invention to provide an improved process for obtaining steroids from urine.

It is an additional object of the invention to provide an improved process for obtaining steroids from mammalian urine.

It is still a further object of the present invention to provide an improved process of obtaining steroids from horse urine.

It is yet another object of the invention to provide an improved process for obtaining steroids from mare's urine.

Still another object of the invention is to provide an improved process for obtaining steroids from pregnant mare's urine.

Still a further object of the present invention is to provide an improved process for obtaining estrogens from urine.

An even further object of the invention is to provide an improved process for obtaining conjugated estrogens from urine.

A preferred object of the invention is to provide an improved process for obtaining conjugated estrogens from pregnant mare's urine.

Another highly preferred object of the present invention is to provide a conjugated estrogen product having a reproducible, controlled content of conjugated estrogen species.

It is another object of the invention to provide a conjugated estrogen product having a product consistency from batch to batch that is improved over that existing in the PREMARIN marketed product as of the filing date of the present application.

It is still a further object of the invention to provide a process for obtaining a conjugated estrogen containing product having a reproducible, controlled content of conjugated estrogen species.

It is still a further object of the invention to provide a process for obtaining a conjugated estrogen containing product having a product consistency from batch to batch that is improved over that existing in the PREMARIN marketed product as of the filing date of the present application.

It is still a further object of the invention to provide a process for solid extraction of steroids from urine.

It is yet a further object of the invention to obtain a natural conjugated estrogen mixture containing a set profile of conjugated estrogen constituents and concentrations, which has been pre-defined.

Still other objects of the invention will be recognized by those of ordinary skill in the art.

BRIEF SUMMARY OF THE INVENTION

These and other objects of the invention are surprisingly achieved by a process in which urine is optionally filtered to remove solid extraneous matter and optionally treated so as to reduce the phenolic content of the urine followed by filtration to give a reduced phenolic content urine fourth liquid remainder. The fourth liquid remainder (when phenolic content reduction is used) or the urine (when phenolic reduction is not used earlier) is then optionally subjected to a solid extraction of certain non-steroidal organic components (with some extraction of conjugated estrogen components estrone and equilin and little extraction of most other desired steroids) by a non-ionic resin to yield a first liquid remainder containing the bulk of the desired steroids. However, since more than an insignificant amount of equilin and estrone (when present in the urine) are removed by this resin, recovery thereof is generally desirable. The first liquid remainder is then subjected to further extraction of a first group of steroids (which, in the case of pregnant mare's urine as the urine source, generally includes equilin, estrone, 17α-estradiol, 17α-dihydroequilin, 17α-dihydroequilenin, and 17β-dihydroequilenin) therefrom by a second suitable resin (to yield a second resin laden with the first group of steroids and a second liquid remainder). The second liquid remainder is subjected to a further solid phase adsorption of a second group of steroids (which, in the case of pregnant mare's urine as the urine source, generally includes $\Delta^{8,9}$ dihydroestrone, equilenin, 17β-dihydroequilin, and 17β-estradiol) therefrom by a third suitable resin (to yield a third resin laden with the second group of steroids and a third liquid remainder). The second and third resins laden with their respective steroids are then eluted and the eluates are collected separately and optionally subjected to further purification and chromatographic separations, with each resulting separate collection being analyzed for the steroid content thereof. The separate analyzed materials are dried and stored for recombination in an appropriate manner based on a collection of data from multiple extraction lots so that the ultimate product has very nearly the same steroid components and concentrations from batch to batch. When the steroids are components of or component mixtures of conjugated estrogens, they may be recombined in a manner such that the sodium salts of the specific sulfated estrogens and the concentrations thereof are essentially constant from batch to batch and such products have substantially less variability than that present in the marketed PREMARIN product as of the filing date of the present application. The isolated steroids or steroid mixtures can be recombined in other proportions to meet other desired product profiles and for other uses that will be apparent to those of ordinary skill in the art. Additional steroids are recovered or recoverable from the first resin after separation from the first liquid remainder as well as from the portion that contains the phenolics in the phenolic reduction step, and other steps.

DETAILED DESCRIPTION OF THE INVENTION

Figure 1:
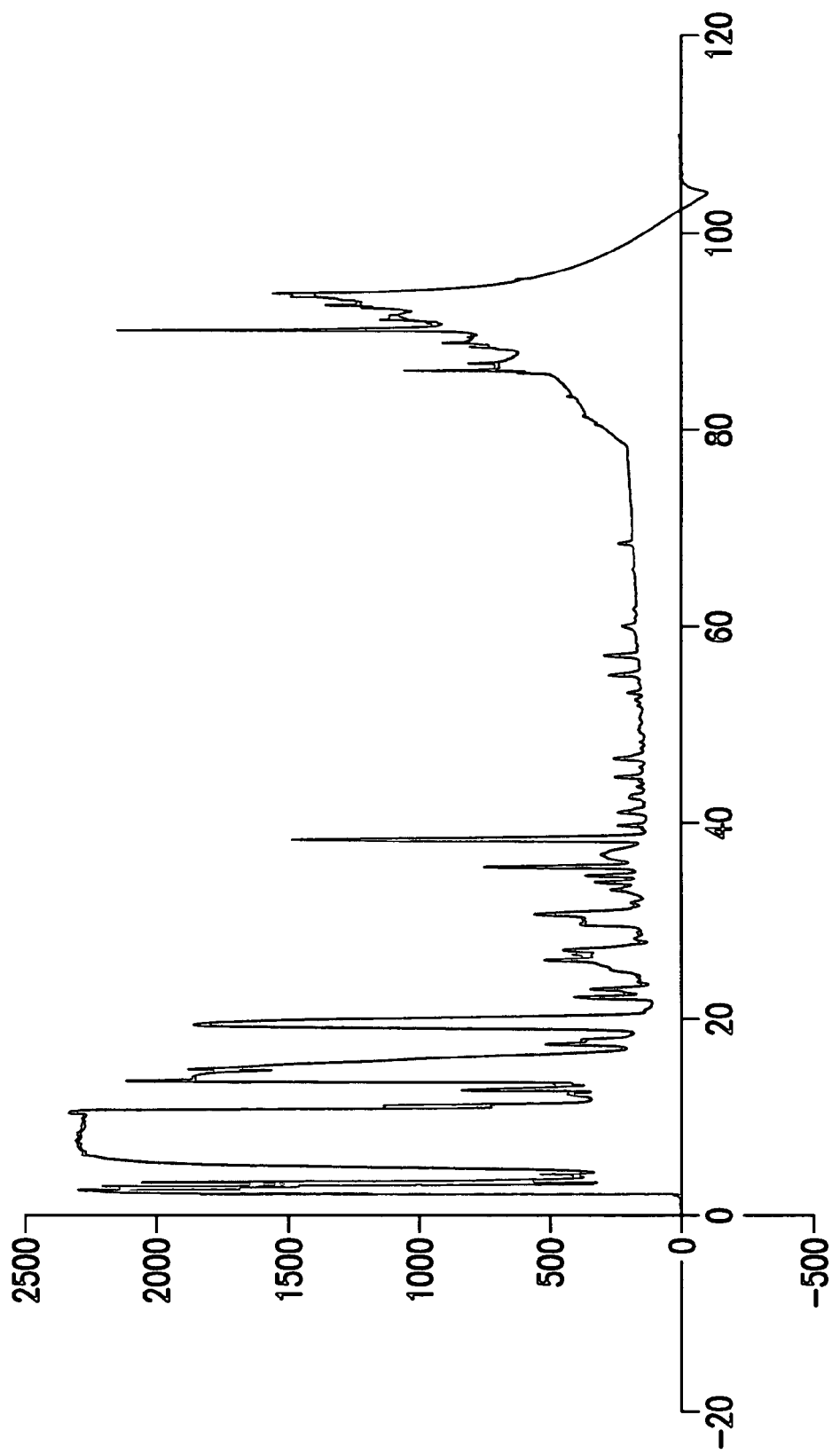
FIG. 1 is an HPLC (of over 100 minutes) of a first representative lot of filtered, but otherwise untreated, pregnant mare's urine.
Figure 2:
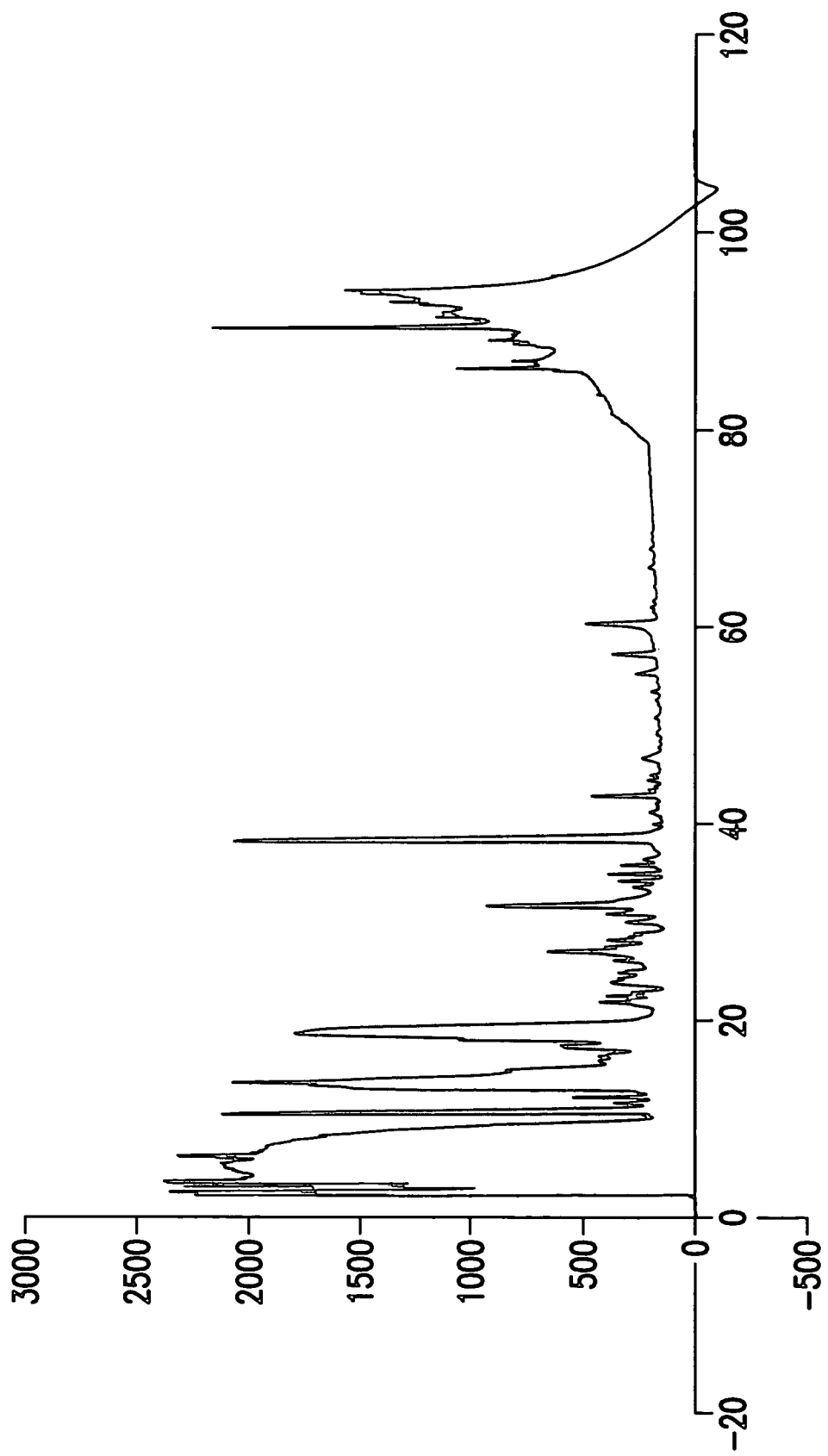
FIG. 2 is an HPLC (of over 100 minutes) of a second representative lot of filtered, but otherwise untreated, pregnant mare's urine.
Figure 3:
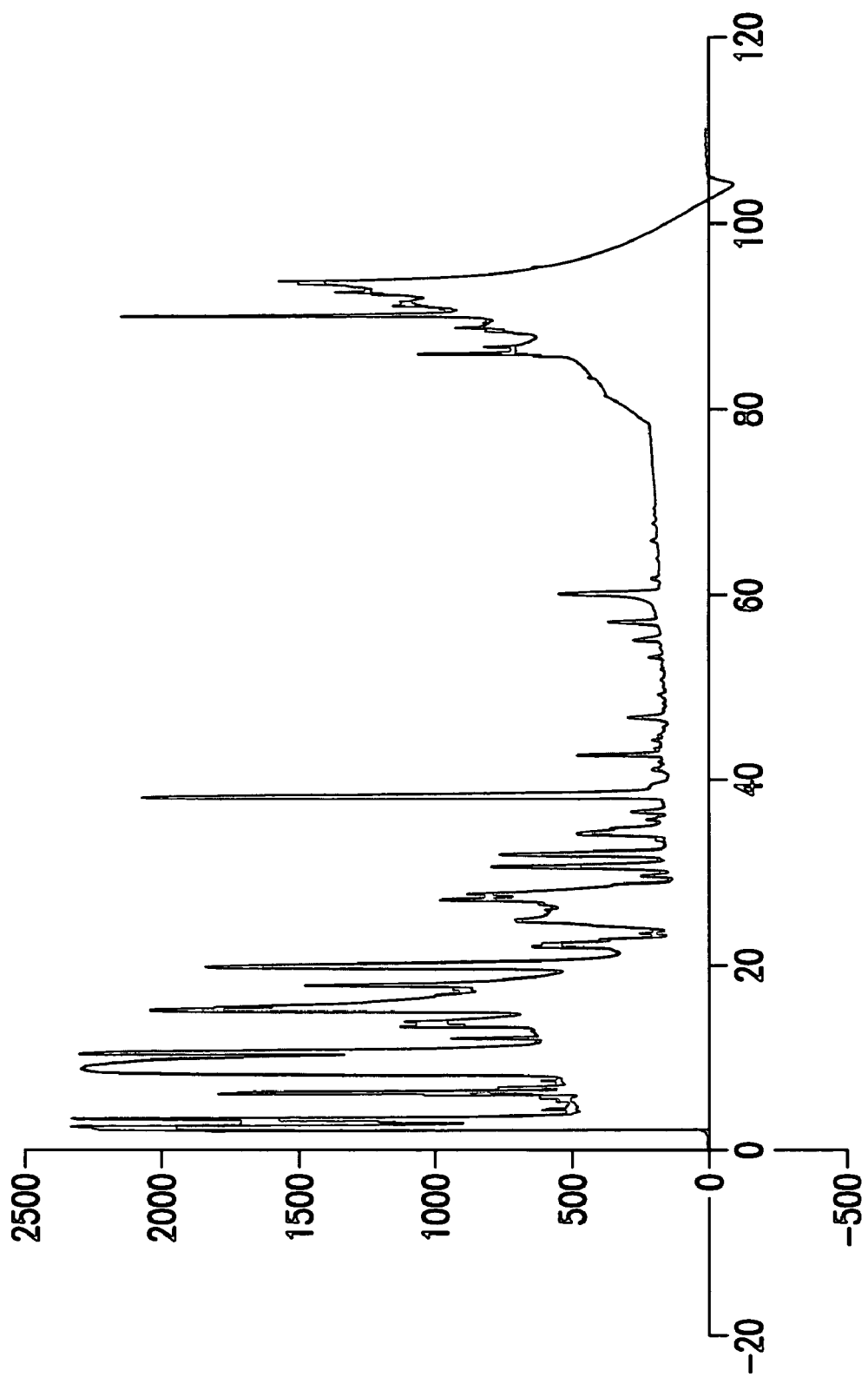
FIG. 3 is an HPLC (of over 100 minutes) of a third representative lot of filtered, but otherwise untreated, pregnant mare's urine.
Figure 4:
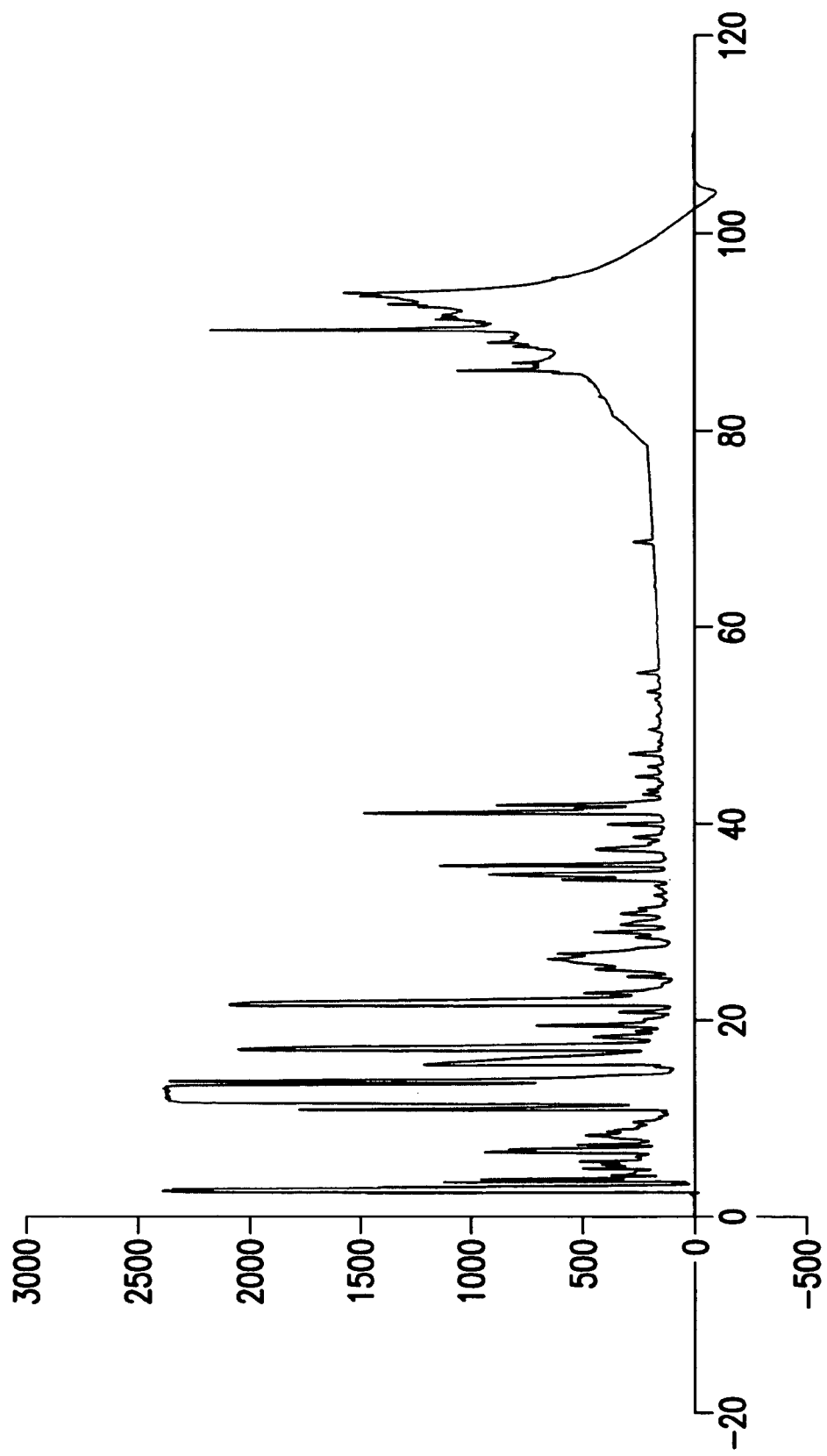
FIG. 4 is an HPLC (of over 100 minutes) of a fourth representative lot of filtered, but otherwise untreated, pregnant mare's urine.
Figure 5:
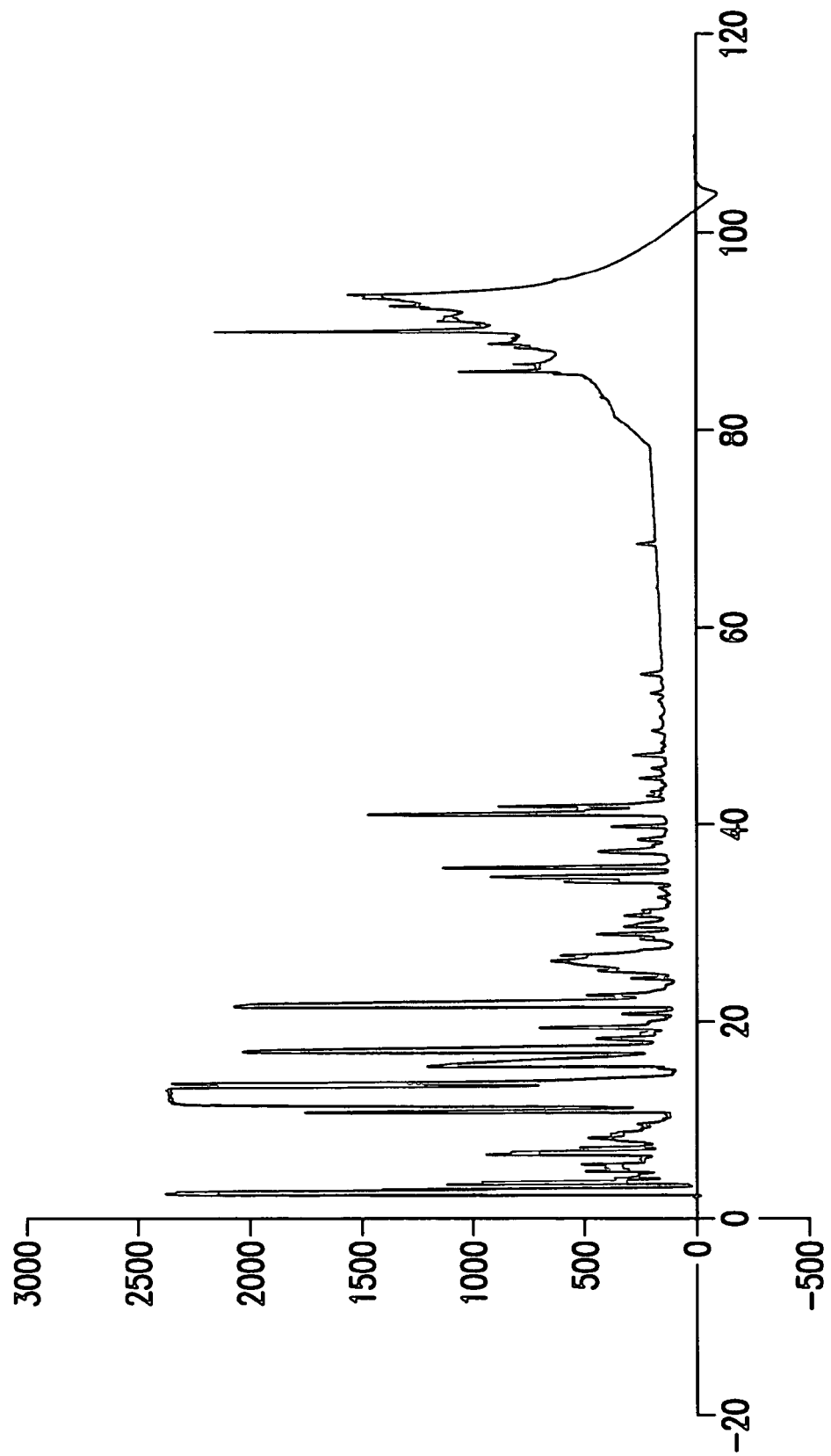
FIG. 5 is an HPLC (of over 100 minutes) of a fifth representative lot of filtered, but otherwise untreated, pregnant mare's urine.
Figure 6:
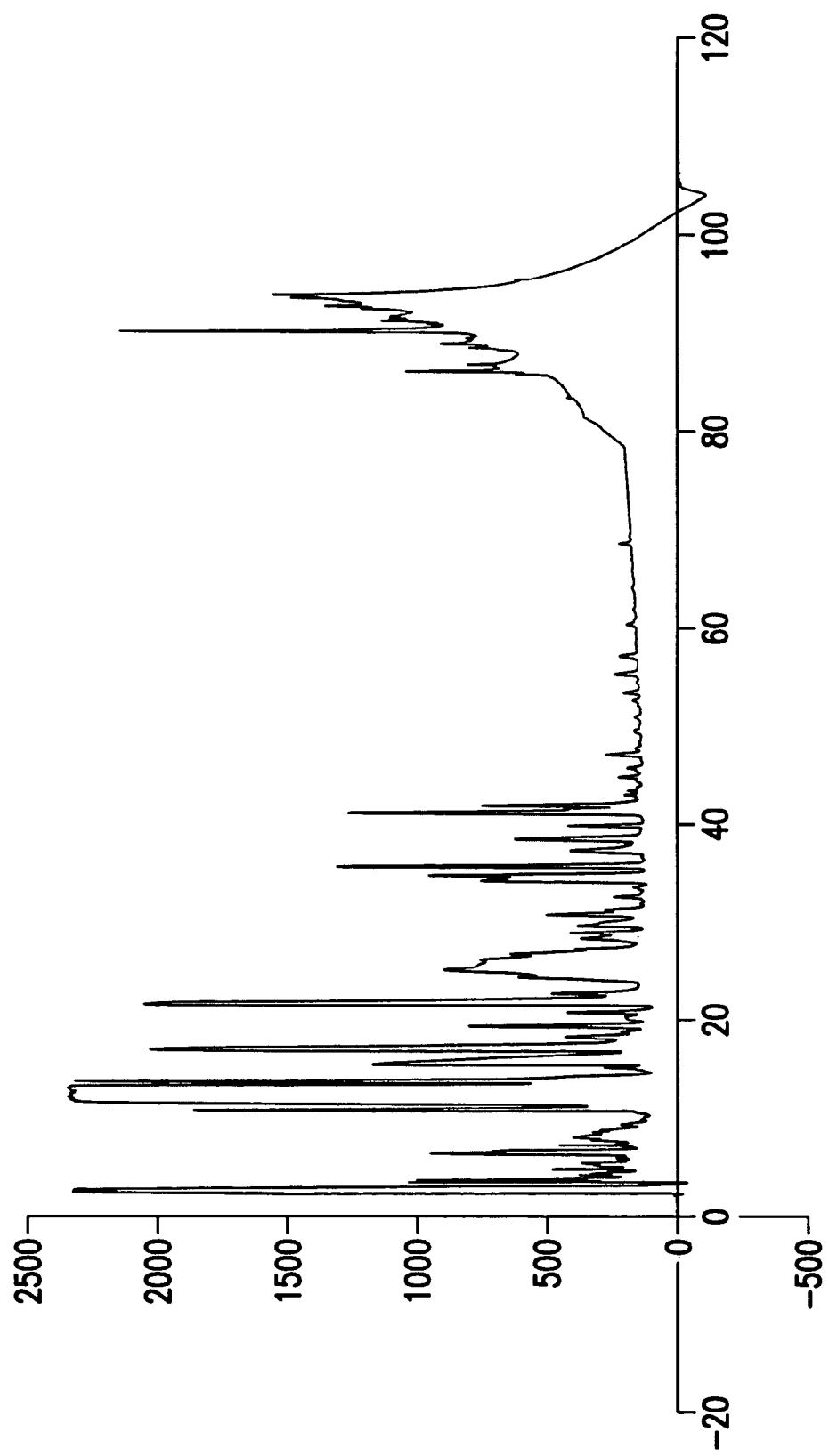
FIG. 6 is an HPLC (of over 100 minutes) of a sixth representative lot of filtered, but otherwise untreated, pregnant mare's urine.
Figure 7:
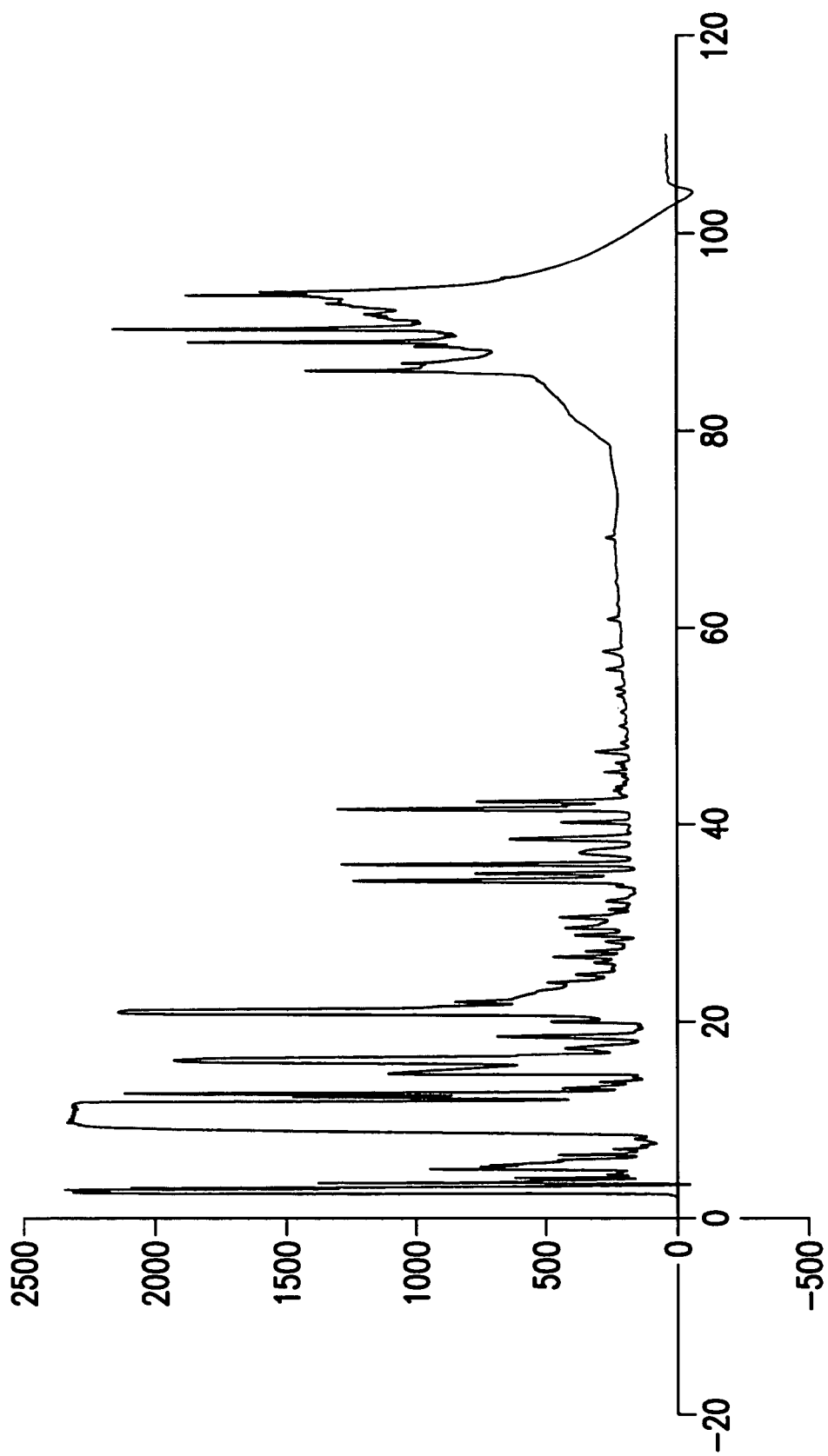
FIG. 7 is an HPLC (of over 100 minutes) of a seventh representative lot of filtered, but otherwise untreated, pregnant mare's urine.
Figure 8:
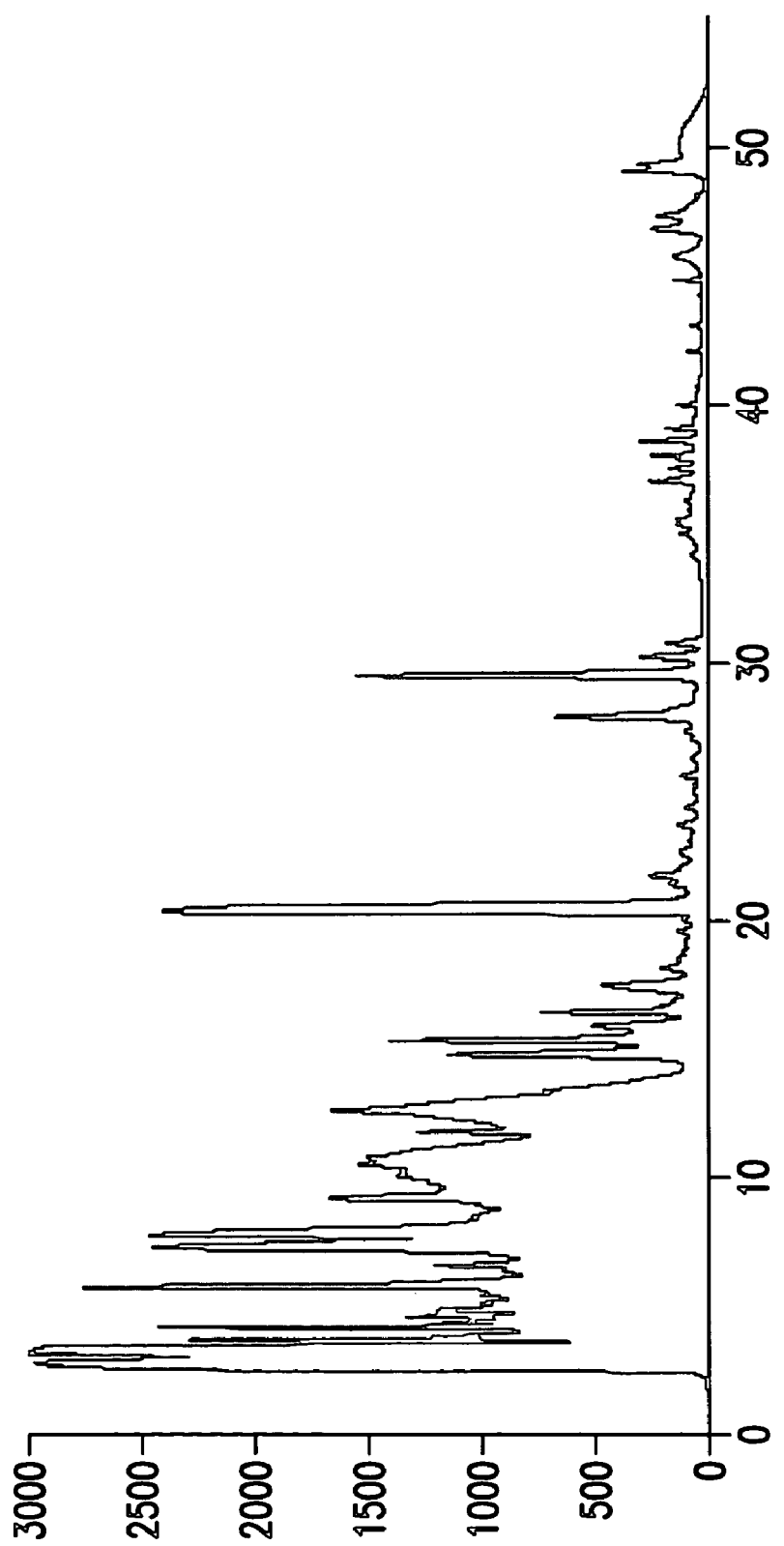
FIG. 8 is an expanded scale HPLC (of about one hour) of yet another representative lot of filtered, but otherwise untreated, pregnant mare's urine sample.

The present invention is a method of extracting steroids, especially those components of natural conjugated estrogens from urine. Urine from any source can be used, but preferably mammalian urine is used. Depending upon the steroids desired, certain species, a certain gender, and certain life stages may be preferable over others. Where generally androgenic steroids are desired, urine from males may be preferable. Where estrogens are preferred, urine from females may be preferred. In meeting predetermined specific steroid content, especially in mixed steroid preparations, the urine may be preferable from certain species since some steroids are produced in larger quantities in a limited number of species, but blending of urine (from different species) to be extracted or blending extracts of urine (from different species) in meeting the predetermined product criteria is also within the scope of the present invention. Of note are the estrogenic compounds (including but not limited to) equilin, 17β-dihydroequilin, estrone, 17β-estradiol, equilenin, 17α-dihydroequilenin, and 17β-dihydroequilenin, which are produced in reasonably recovered quantities in pregnant mares. Thus, where these estrogens are desired to be recovered, pregnant mare urine is the preferred urine for use in the invention. Nonetheless, the present invention includes the use of urine from any source, preferably mammals, more preferably large mammals, even more preferably domesticated large mammals. Most preferably, the large mammals include, without limitation, typical farm mammals, including, without limitation, horses, cattle, pigs, etc., with horses being highly preferred. Mares are especially preferred for estrogenic steroid sources, with pregnant mares being most highly preferred as the source of high estrogenic steroid content urine, and most especially when the pre-determined product profile to meet is that of a conjugated estrogen containing product.

Pregnant mare's urine varies in its steroid content, especially in its conjugated estrogen content depending upon the breed of horse, its feed, and the point in the pregnancy when the urine is collected. Yet, the conjugated estrogen content can almost always be described as a complex mixture with a few specific conjugated estrogen constituents being present in a larger concentration (such as estrone and equilin, each present in conjugated form as the sodium sulfate salts) and a larger number of estrogens present in a much smaller concentration (17α-estradiol, $\Delta^{8,9}$-dihydroestrone, 17β-dihydroequilin, 17β-estradiol, equilenin, 17α-dihydroequilenin, 17β-dihydroequilenin, and others—each present in conjugated form as the sodium sulfate salt). The non-estrogenic steroid content from this urine source is also a complex mixture, but generally at lower levels. Compare FIGS. 1-8 for a sense of the variability in steroidal contents between lots of urine from pregnant mares that was not processed except for gross filtration.

The invention is in the method of extracting the complex mixture of steroids found in the particular urine source used into simpler mixtures and/or into individual components (compare FIGS. 8-10), and then, based on a pre-defined reference standard definition, recombining various portions in varying amounts to meet the definition of the reference standard. In the course of preparing such simpler mixtures or isolation of individual desired components for meeting the desired pre-determined criteria, a number of additional steroids that are not relevant to the object of meeting the predetermined mixture criteria are or can be recovered from portions that would otherwise be considered discard material. Recovery of steroids not important to the object of meeting the preset criteria of the moment and/or recovery of minor amounts of the desired steroids (which may not have been recovered otherwise) from the portions that would otherwise be considered "discard material" is also deemed to be part of the present invention.

By reducing the complex mixtures of steroids down to much simpler mixtures and/or isolated compounds, the qualitative and quantitative steroid content of each component can be stored in a database and specific amounts of different mixtures and/or isolates can be recombined to meet pre-defined qualitative and quantitative criteria so as to achieve a highly reproducible product having a consistent set of steroids in the mixture as well as a consistent concentration of each steroid from batch to batch. Nowhere is this more in need than in the case of conjugated estrogens, which is the most highly preferred embodiment of the invention. While the bulk of the remainder of this specification will deal with conjugated estrogens from pregnant mare's urine, those of ordinary skill will readily appreciate the other steroids that can be isolated and from what stages of the process as set forth below, as well as the modifications that need be taken when using urine from other sources, especially when using urine from male sources.

Figure 11:
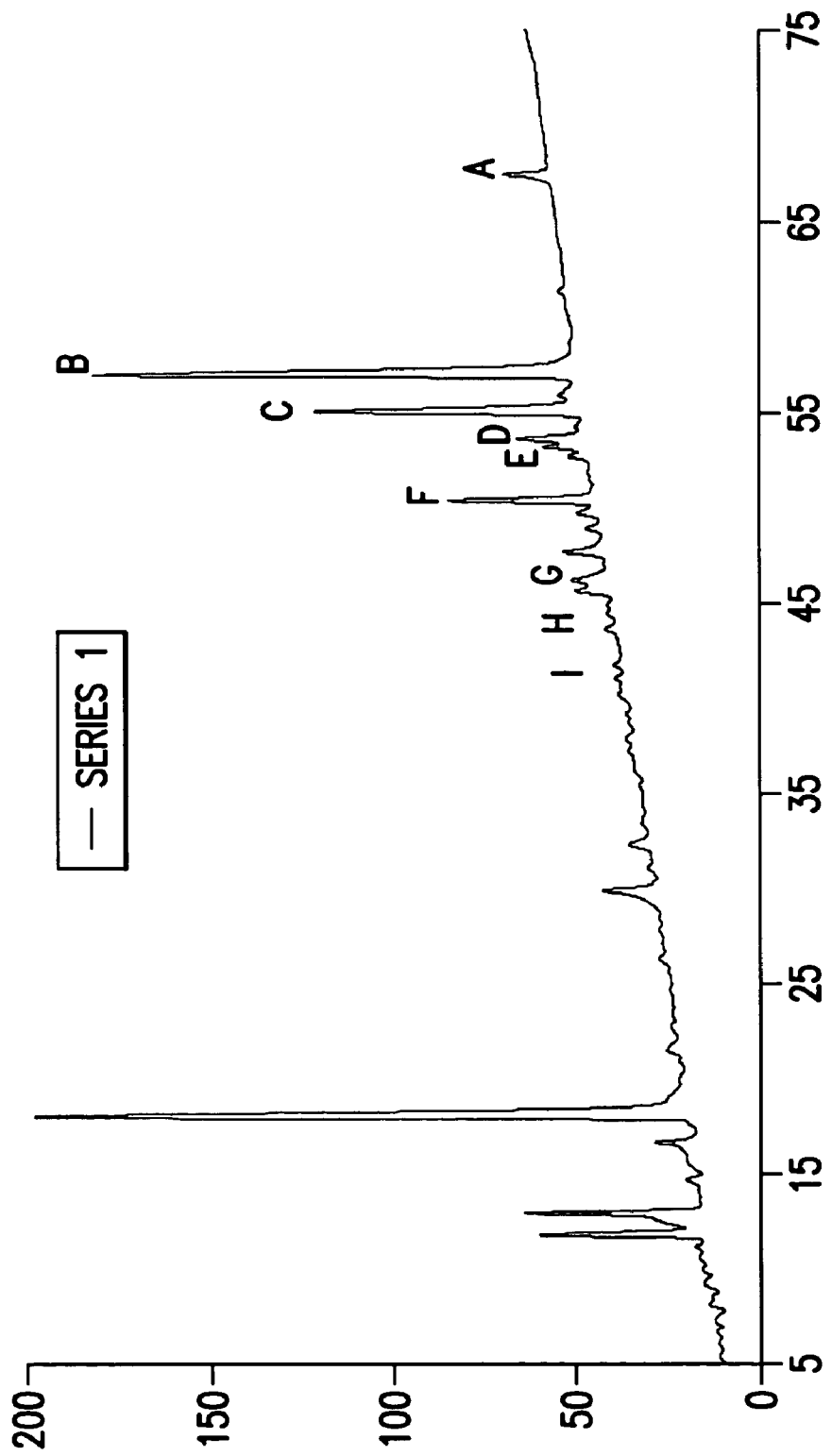
FIG. 11 is a comparison HPLC during the first 75 minutes of a methanol extract of a single lot of Premarin tablets. 9 peaks are identified for comparison with FIG. 10.

Conjugated estrogens are currently marketed under the name PREMARIN, a product which is a natural mixture of the sodium salts of sulfate esters of estrogens found in pregnant mare's urine (see FIG. 11). However, as stated above, depending upon the feed, the breed of horse, the stage of pregnancy, even the time of year, this natural mixture varies considerably from urine sample to urine sample, both in the particular estrogens that are present as well as the concentrations of the estrogens that are present. Thus, breaking down of the steroid content of the urine into simpler mixtures or into individual components and recombining different isolates to meet a defined criteria results in a more consistent and uniform product, having less chance for the presence of extraneous steroids and therefore (a) has less chance of having adverse effects, and (b) provides a simpler basis for quality control of the product than is possible with the currently marketed PREMARIN product. PREMARIN contains a mixture of estrogenic substances obtained exclusively from natural sources. It is a mixture of sodium estrone sulfate and sodium equilin sulfate and at least the following 8 components (present as the sodium salt of the respective sulfate ester): 17α-dihydroequilenin, 17α-estradiol, $\Delta^{8,9}$-dihydroestrone, 17β-dihydroequilin, 17β-estradiol, equilenin, and 17β-dihydroequilenin. It also has a large number of other estrogenic steroids in small concentrations.

While not required, the following two optional steps (refrigeration and placing under an inert atmosphere) are beneficial for improving the stability of the steroids, especially the sulfated esters of the steroids, from the point of collection from the source through transport to a processing facility and storage at such processing facility. It should be noted that where the free steroids are desired rather than esterified steroids, refrigeration is not as great a concern. When warmer temperatures are involved, the esterified steroids first typically convert over to the non-esterified counterpart and then degrade. The unesterified steroids are recoverable if desired (as seen in later stages below) and may be converted back to esterified steroids if so desired. Esterified steroids that are not sulfate esters, if recovered, may be converted to free steroids and then converted to sulfated steroids. These conversions may be performed at any time in the process, but are preferably conducted after most of the desired existing sulfated steroids have been separated therefrom, thus simplifying the conversion processes.

First, once urine is collected, esterified steroids, particularly conjugated estrogen components, contained therein have a relatively short half life of about 3-4 days if unrefrigerated. Therefore, a substantial amount of the esterified steroid content (especially conjugated estrogen constituent content) can be lost if processing cannot be started immediately. The half-life increases sharply with decreasing temperature so that when refrigerated at about 2° C., the esterified steroids (especially esterified estrogens and conjugated estrogen constituents) in the urine are stable for about 4 months or longer. Thus, in order to maximize yield of esterified steroids (particularly conjugated estrogen constituents)/unit of urine processed, unless processing can be started immediately, the urine should be refrigerated for as much of the time as possible until processed.

Second, esterified steroids, especially conjugated estrogen constituents, are subject to oxidation and therefore, it is preferable to keep the collected urine under an inert atmosphere, such as nitrogen, in order to further maximize the recovery of desired steroids (especially conjugated estrogen constituents)/unit of urine processed. The need to place the urine under inert atmosphere is less urgent than the impact of temperature and therefore need not be done during the entire period before processing begins. However, it is best to keep the collected urine under an inert atmosphere when the collected urine is being stored for any extended period of time. Generally this means that no inert atmosphere is used at the farm collection point or in the transport vehicle tanks, but once delivered to the processing facility and being stored in tanks there, an inert atmosphere is used to purge the atmosphere of the headspace in the storage tanks. This compromise is based on the economics and feasibility of placing the collected urine under inert atmosphere prior to reaching the processing facility and the losses resulting from oxidation.

Nonetheless, the best means to assure the greatest yield of steroids (especially conjugated estrogen constituents)/unit of urine processed is to place the collected urine under an inert atmosphere as soon as possible. When long term storage of the urine is desired it is further preferable to add a significant amount of water-soluble alcohol to the urine, generally so that the alcohol content of the resulting solution is about 10 to about 50%, preferably about 20 to about 40%, more preferably about 25 to about 35%, and most preferably about 25%. Generally, monohydric alcohols of 1 to 3 carbons are used, preferably methanol, ethanol, or isopropanol, most advantageously methanol or isopropanol.

Additionally, in order to improve pumpability between collection point, transport vehicle, and processing facility, a gross filtration step to remove large foreign debris that might interfere with transfer of the collected urine between the collection point and the transport vehicle or the transport vehicle and the processing facility, is preferably used in the collection process or in the transfer from the collection point and the transport vehicle as appropriate. Generally, the gross filtration is done when first collecting the urine, but it may be done at later stages and even at the processing facility as convenient. For the gross filtration step, a filter of about 1 µm to about 15 µm, preferably about 1.5 µm to about 10 µm, more preferably about 1.75 µm to about 5 µm, most preferably about 2 µm pore size is suitable. However, larger or smaller pore filters may be used and this filtration may be in a single filtration or in a series of multiple filtrations of successively narrower pore filters as is convenient. Any filtration method may be used, and other separation techniques in place of filtration to remove particulate matter may be substituted for filtration as may be convenient for the user. An example of such alternate separation techniques may be, but is not limited to, decantation. Nonetheless, filtration is generally the most efficient manner of separating the particulate matter from the urine and is therefore preferred.

Whether or not the urine has been filtered earlier, the urine is further optionally treated to remove mucilaginous materials and extraneous solids. Typically, the solids and mucilaginous materials are allowed to settle and then separated by known separations techniques such as decanting, separation, and/or filtration. Preferably at least filtration is used. A sand bed, for example, may serve as a separating apparatus, or a commercially available separator, e.g. nozzle separators or chamber separators may be used. Filter presses, bag filters, and centrifugation are generally known in the art and are also suitable for use in separating extraneous solids and/or mucilaginous materials from the urine in the practice of the present invention. Microfiltration and ultrafiltration apparatus may be used, and if used, it is possible to obtain a substantially bacteria-free and virus-free resulting solution. This is particularly advantageous if the urine is to be stored for any significant amount of time before further processing. Generally though, basket filters are typically preferred for convenience purposes and such basket filters having pore sizes of about 0.05 µm to about 15 µm may be used. Most preferably a series, typically 2-3 are used (although more or fewer may be used) having serially smaller sized pores. In one embodiment the first basket might have pores of about 5 to about 15 µm with a preferred size of about 5.0 microns and the second basket filter might have pores of about 0.05 µm to about 0.5 µm, with a preferred size of about 0.1 µm or about 0.2 µm. The primary reason for using a series of successively smaller filters is to prevent clogging of the smaller filters and to thereby increase efficiency of the entire process by maintaining flow rates and decreasing down time due to filter replacement. In addition, filters having pores below about 1 µm begin to filter out materials which interfere with the absorption of the esterified steroids (preferably conjugated estrogens) in the later resin solid extraction steps and also increase the life of the resin. Using a smaller pore size such as going from 1 µm to 0.1 µm would increase the resin life by about 50%. Thus, when using filters of finer pore sizes, the efficiency of the process increases in terms of esterified steroids (preferably conjugated estrogens) recovered. For example, in one recovery process from pregnant mare's urine where the smallest filter used is 1 µm, recovery of conjugated estrogens is about 50%. In the same process except that the smallest filter used is 0.1 µm, the useful life of the resins increases by about 86%. However as pore size of the smallest filter used drops below about 0.05 µm to about 0.1 µm, the filters begin to filter out some of the esterified steroids (including some of the conjugated estrogens) as well, although the loss of the desired steroids is not proportional to relative concentration of the steroids present. Therefore, where the major loss of esterified steroids is in particular esterified steroids that are not absolutely needed, even finer pore sized filters may be employed in the filtration steps. However, where esterified steroids particularly the estrogenic substances) that are desired are significantly lost at smaller filter sizes, one should increase the size of the smallest filter used until an appropriate balance is reached between steroid loss and recovery efficiency improvements. Generally filter pore sizes in the 0.05 µm to 0.1 µm range are suitable for efficient recovery of desired estrogenic substances in the production of a conjugated estrogen product intended to be therapeutically substitutable for PREMARIN. Adjustment of these sizes to reflect other economic impacts as well as for obtaining different steroidal substances will be apparent to those of ordinary skill and such variations are deemed to be within the scope of the present invention. A flow rate of between 0.25 and 2, preferably between about 0.5 and 2, gallons per minute is suitably used, and this may be matched to the flow rates within the subsequent columns so as to result in a continuously flowing system, which only need be halted to replace resins or filters when needed, and where more than one column of each type and filter of each type is set up in parallel, the system can be switched between parallel set ups without stopping the system, thereby allowing replacement of any resin or filter without halting the fluid flow. Any kind of pump may be used, but positive displacement pumps are preferred to minimize aeration and further reduce the possibility of hydrolysis.

When desired, one or more of the filters may be coated with diatomaceous earth. If desired, preservatives, germicides, bacteriocides, and/or anthelmintics can be added to the urine, but only if such materials do not find their way into the steroidal mixtures recovered from the resins.

If desired, the urine can be optionally concentrated before or after the above referenced separation of the mucilaginous materials and extraneous solids. The concentration step may also take place before or after any pH adjustment or buffering, discussed below. Concentration of the urine can be carried out by known membrane filtration. For example, when using a nanofiltration membrane, a practically loss-free concentration of the esterified steroid (especially conjugated estrogen) content of the urine can be achieved with simultaneous removal of up to 50% by weight of the lower molecular weight urine contents. Urine retentates concentrated by factors of 7 to 10 over the original urine can be obtained in this manner, thus allowing one to process $1/7^{th}$ to $1/10^{th}$, respectively of the volume of original urine.

Also, the urine (either before or after removal of the mucilaginous materials and extraneous solids), is optionally pH adjusted or buffered to a pH in excess of at least 8.0. Generally pregnant mare's urine has a pH in the range of 8 to 9.5, so that pH adjustment or buffering is not critical. However, since the esterified steroids (especially conjugated estrogen constituents) are stabilized in the pH range of about 8.0 to about 12, preferably about 8.25 to about 10, more preferably about 8.5 to about 9.6, it is preferably to assure that the pH is in this range. Urine from other sources may have different pH's and use thereof may require pH adjustment into this range for stabilization and recovery of the esterified steroids. However, if non-esterified steroids are the desired endpoint of the process, the pH adjustment may not be necessary, and in fact, a slight acidification may be desired. Furthermore, where the subsequent conversion of free steroids to the sulfate esters is not of concern, the pH adjustment is not necessary as any desired steroids that are free steroids due to the pH effect on the originally present sulfate esters can be converted back to their respective sulfate esters in subsequent processing steps as seen below.

While pH adjustment to a pH over 8 can be had with any alkaline material that does not substantially interact with the steroids of concern, a buffer system is preferred. Suitable alkaline pH adjusters and buffers include, but are not limited to, alkali metal, alkaline earth metal, ammonium and quaternary ammonium compounds (including without limitation sodium, potassium, magnesium, calcium, and ammonium) hydroxides, carbonates, bicarbonates, sulfates, bisulfates, sulfites, bisulfites, phosphates, and monohydrogenphosphates. Quaternary ammonium compounds may include any quaternary ammonium compound that does not substantially adversely affect the desired steroids. Variable effects of the quaternary ammonium compounds on the resins' efficiency or useful life may be acceptable based on economic factors, but preferably do not substantially adversely affect either the various resin efficiencies or useful lives. Preferable quaternary ammonium compounds for this purpose include, without limitation, (1) N—$C_{6-10}$aryl-loweralkyl-N,N-diloweralkyl-N-alkyl ammonium halide, preferably N-phenyllower alkyl-N,N-diloweralkyl-N-alkyl ammonium halide, more preferably N-benzyl-N,N-dimethyl-N-alkyl ammonium halide, even more preferably N-benzyl-N,N-dimethyl-N—$C_{8-18}$alkyl ammonium halide, most preferably benzalkonium chloride (where each lower alkyl is independently $C_{1-3}$alkyl, preferably methyl, ethyl, propyl, or isopropyl; the alkyl without designation of lower indicates an alkyl group of at least 6 carbons, preferably at least 8 carbons, and not more than about 22 carbons, preferably not more than 20 carbons, more preferably not more than 18 carbons; halide is chloride, fluoride, bromide, or iodide, preferably chloride or bromide, more preferably chloride) or (2) 6 to 14 member nitrogen containing heteroaryl having a higher alkyl substituent on one or more of the nitrogen atom(s) halide, preferably a 6 to 14 membered heterocycle having a single hetero atom which is nitrogen and having a higher alkyl group substituted on the heteroatom halide, more preferably a pyridine ring having a higher alkyl substituent on the nitrogen atom thereof, still more preferably higher alkyl-pyridinium chloride, even more preferably cetyl pyridinium chloride (where higher alkyl is a 10 to 22 carbon alkyl, preferably 12 to 20 carbons, more preferably 14 to 18 carbons, most preferably 16 carbons; and preferably the higher alkyl chain is straight). Preferably, the pH adjuster or buffer is a buffer, most preferably sodium sulfate or sodium sulfite, or sodium sulfite/sodium bisulfite mixture. The pH adjuster or buffer is best used in the smallest reasonable amounts so as to minimize the impact on the efficiencies of the resins, especially the efficiency of the cationic exchange resin.

In a second alternative embodiment, the pH of the urine is not adjusted and not buffered, especially when the urine used is pregnant mare's urine. Avoiding the pH adjuster or buffer is advantageous in that it will not alter or add counterions to possibly occupy sites on the resin interfering with the extraction. However, since pH changes can affect the resin's ability to extract esterified steroids relative to other products and even between the various esterified steroids, allowing the pH to be that which the urine naturally has introduces some limited variability into the process, especially if urine sources are varied between species. Thus, the choice of whether to use a pH adjuster or buffer or not to use one is a compromise between esterified steroid stability and extraction efficiency and the economics associated therewith. Such balancing of factors is well within the ordinary skill in the art and variations will be appreciated by those of ordinary skill.

Preferably, when the pH adjustment or buffer is used, the pH is adjusted or buffered before either any filtration mentioned above and before any phenolic removal below. This is because having the pH in the stated range stabilizes the esterified steroids and breaks down certain proteins and blood products which may be present therewith, making it easier to filter out the breakdown products. Thus, it is best to use a filtration step after the pH adjustment; however, the pH adjustment or buffering, when used, may take place after the filtration step if desired.

Whether the urine has been optionally pH adjusted and/or optionally filtered or not, it is then processed to reduce, preferably completely eliminate the phenolic contents thereof. Urine has, in addition to the steroids, urea, and other typical urine constituents, a number of phenolic compounds, such as cresols. These phenolic constituents interfere with the absorption of the steroids on the various resins and therefore reduce the efficiency of the resins as steroid extracting agents. Therefore, before extraction of the steroids, the phenolic content of the urine is preferably reduced, although the balance of the method can be used without the phenolic content reduction at this point, and if these phenolics are not removed at this stage, they will have to be removed later anyway. Thus, reduction, preferably elimination, of the phenolic constituents is most preferably done before use of the steroid extraction resins. This reduction in phenolic content can be accomplished in any manner known in the art and is preferably by (a) contacting the urine with a resin capable of extracting phenolic urine constituents without extracting significant amounts, preferably without extracting any, of the steroids, preferably without extracting the esterified steroid constituents, most preferably without extracting the conjugated estrogen constituents of the urine or (b) use of a non-porous silicone membrane such as those described in US 2003/0215953 (incorporated herein in its entirety by reference). Preferably, a phenolic constituent absorbing resin is used. Either of these phenolic constituent separation techniques results in a reduced-phenolic content urine, preferably a phenolic-constituent free urine (hereinafter, "fourth liquid remainder") and a phenolic containing extract. As a phenolic constituent absorbent resin, it is preferable to use weakly anionic exchange resin materials.

For purposes of the present invention, "weakly anionic exchange resin" materials is intended to mean materials that when placed in pH 8.5 water demonstrate the capability of being able to weakly exchange anions. That is they carry functional groups that form salts with anions and when in pH 8.5 water are in at least two forms, one having a positive charge and one having a less positive charge (generally neutral) with the two forms being in equilibrium in a given ratio. Given that the resin is polymeric and will contain multiple repeating units having the "weakly anionic exchanging" functional group, the same molecule may and generally will contain both forms of such functional group. Such resins may contain more than one type of weakly anionic exchanging functional group. Such multiple functional groups can be for example, without limitation, quaternary ammonium groups, dimethylamino groups, dimethylethanolbenzyl ammonium groups, and polyamine groups. The weakly anionic exchange resin materials include, but are not limited to, polymeric backbones selected from the group consisting of polystyrene-divinylbenzene, polyacrylate, polymethacrylate, poly(acrylate/methacrylate), polyacrylamide, polyphenolics and copolymers thereof where such backbones have side chains that include one or more of the aforementioned weakly anionic exchange groups. A highly preferred embodiment utilizes a polystyrene-divinylbenzene resin that is approximately 12% cross-linked and has tertiary ammonium side chains (maintained in the free form), which resin is commercially available under the name Dowex® XAD2 (available from DOW). Other weakly anionic exchange resins suitable for use in the present invention include, without limitation, those available from Itochu such as for example: Diaion SA10A. SA11A, SA12A, NSA100, SAF12A, HPA 25, PA 306S, PA308, PA312, and PA316 (each being a polystyrene backbone having a trimethylammoniummethyl side chain with a chloride counterion); Diaion SAF12 OH (being a polystyrene backbone having a trimethylammoniummethyl side chain with a hydroxide counterion); Diaion SA20A, SA21A, HPA75, PAF418, PA408, PA412, and PA418 (each having a polystyrene backbone with 2-hydroxyethyl-dimethylammoniummethyl side chains with a chloride counterion); Diaion SA20A OH (having a polystyrene backbone with 2-hydroxyethyl-dimethylammoniummethyl side chains with a hydroxide counterion; Diaion DCA11, and WA30 (each having a polystyrene backbone with a dimethylaminomethyl side chains); Diaion TSA1200 and RSA1200 (each having a polystyrene backbone with 4-(trimethylammonium)but-1-yl side chains with a hydroxide counter ion); Diaion CR20, WA20, and WA21j (each having a polystyrene backbone and a polyethyleneiminemethyl side chain); PrepEx DEAE (having a 2-diethylamino-1-hydroxyethyl side chain); Sephabeads FP-DA13 (having a diethylamino side chain); Sephabead FP-HA-13 (having a 6-aminohexylamino side chain); Diaion CRB01, CRB02 (each having a polystyrene backbone and a 2,3,4,5,6-pentahydroxyhexyl-N-methylaminomethyl side chain); and Diaion WA10 (having a polyacrylamide backbone and a dimethylaminoalkylene side chain pendent on the acrylamide nitrogen). Other similar anion exchange resins from other manufacturers will be recognized as suitable in the present invention by those of ordinary skill in the art.

When Dowex XAD2 (a highly preferred anionic exchange resin for the present invention) is used, the fresh resin is prepared for use by first washing with water at about pH 7, then with an aqueous acidic lower alkanol solution, and then rinsing with about 5-7 column or bed volumes of purified water at pH 5-7. The lower alkanol is preferably methanol, ethanol, or isopropanol, and more preferably methanol. Any acid or acidic salt may be used to give the purified water a pH of 5-7, with sulfuric acid, hydrochloric acid, nitric acid, sodium bisulfite, sodium bisulfide, sodium potassium hydrogen tartrate, or potassium phosphate monobasic being preferred. Furthermore, given that pH 5-7 is the desired pH to use, purified water that is allowed to equilibrate with the ambient atmosphere will absorb atmospheric gases to have a pH in this range and can be used as is. A 50:50 vol/vol mixture of methanol and 2% sulfuric acid is especially preferred for the aqueous acidic alkanol solution. Comparable resin preparation methods for other weakly anion exchange resins for use in this step will be known to those of ordinary skill in the art.

While any manner of contacting the urine with the resins below is suitable, use of columns or beds packed with the resin through which the urine will flow is preferred with columns being most preferred. While the following discussion is detailed with respect to the use of columns, those of ordinary skill will be readily able to adjust these details to other suitable resin contacting arrangements and methods. Preferably, the resin is packed in a vertical column of 4-8 inches diameter, preferably about 6 inches in diameter, and about 6-10 feet in length, preferably about 8 feet in length, although other sizes and arrangements are perfectly suitable. Fluid flow may be either with or against gravity as desired and is preferable against gravity, being pumped into the bottom of the column with the effluent being taken off the top. Flow rate is determined by the efficiency of the particular resin for removing the component intended to be removed and preferably by monitoring one or more constituents that are to be removed by the resin and comparing the concentrations in the input to the resin and the effluent from the resin as well as changes between two successive determinations. Suitable measures can be made as desired, but for convenience (balancing the expense and effort of overtesting and the risk of overuse or continued use of saturated resin by undertesting) are preferably made at 2-4 hour intervals, preferably every three hours. Generally flow rates between 0.25 and 1.5 gallons/minute (preferably about 0.3 to about 1.25 gallons/minute, still more preferably about 0.5 to about 1.15 gallons/minute, even more preferably the upper end of each of these ranges is not greater than about 1 gallon/minute) are suitable. For the phenolic removing step (anionic exchange resin) when using a 6 inch by 8 foot column of Dowex XAD2, in a unified system with the non-ionic and weak cationic resins described further below, a flow rate of about 1.8 liters/min (about 0.5 gal/min) has been found suitable and is preferred. Preferably, the urine is maintained at a temperature of about 5° to about 15° C., preferably about 10° C. or about 12° C. during the phenolic extraction stage. Although higher temperatures can be used, higher temperatures begin to negatively impact the esterified steroid (especially conjugated estrogen constituent) content that will ultimately be obtainable from the extraction process. After the reduced phenolic content urine is separated from the phenolic materials, the phenolic reduced urine may be concentrated if so desired. Otherwise it is either stored for further processing at another time or immediately processed further. Optionally, the phenolic content of the reduced phenolic content urine can be checked to be sure that the phenolic content has in fact been substantially reduced. If it has not, further contact time or replacement of the resin is necessary. Typically, the resins, when used in the recommended column size and with the recommended flow rate will need to be replaced after processing about 3785 liters (1000 gallons) of fluid. While this is a general rule of thumb, one should rely on the definitive testing (HPLC suggested) of the effluent to determine whether a resin need be changed. Once it is determined that the weakly anionic exchange resin is in need of being replaced, it can be (a) discarded or (b) processed offline to recover the weakly anionic resin and/or the phenolics and any possible steroids removed by the resin. In order to regenerate the resin and/or recover constituents that have been removed by the weakly anion exchange resin, it is first eluted to desorb the extracted materials by contacting the loaded resin with an acidic/alcoholic solution, most preferably a solution of equal volumes of methanol and 2% aqueous sulfuric acid, although virtually any acidic lower alcohol aqueous solution would be suitable. This is continued until no further material is desorbed from the resin, at which time the resin is regenerated by first washing with water at pH 7, then with aqueous acidic lower alkanol solution, and then rinsing the regenerated resin with about 5-7 column or bed volumes of purified water at pH 5-7. The lower alkanol is preferably methanol, ethanol, or isopropanol, and more preferably methanol. Any acid or acidic salt may be used to give the purified water a pH of 5-7, with sulfuric acid, sodium bisulfite, sodium bisulfide, sodium potassium hydrogen tartrate, or potassium phosphate monobasic being preferred. Furthermore, given that pH 5-7 is the desired pH to use, purified water that is allowed to equilibrate with the ambient atmosphere will absorb atmospheric gases to have a pH in this range and can be used as is. If desired, the phenolic materials so removed may be collected and used for other purposes, while the possible steroids removed by this process step can be further processed in accordance with the further invention steps set forth below to recover these additional amounts of steroid.

Optionally, at this point, a further solid extraction is used to remove certain non-steroidal impurities. In one preferred embodiment of the present invention, this step is omitted, while another preferred embodiment of the invention specifically includes this step. When used, this step involves contacting the urine (or the liquid remainder from the previous steps) with a non-ionic size exclusion resin. Preferably, this step is conducted after the phenolic reduction step discussed above and before other extraction steps discussed below. The resin is preferably selected from polymers having a backbone of polyacrylate, polymethacrylate, poly(acrylate/methacrylate) and mixtures thereof. Other backbone polymers are also suitable but less preferred. Additional side groups need not be present. Non-limiting exemplary polymethacrylate resins of this type are Diaion HP1MG and Diaion HP2MG (available from Itochu), the HP2MG having a pore volume of about 1.2 ml/g; a surface area of about 470 $m^2$/g; an average pore radius of about 170 Å; and a minimum effective size of 0.35 mm. Another non-limiting example is Amberchrome G71 (available from Rohm and Haas). The major reason for inclusion of this optional step is the removal of certain undesired impurities that tend to decrease the operating efficiency of subsequent steps. While removing those impurities, the resins of this step also remove more than an insignificant amount of equilin and estrone. However, once loaded, these resins swell much more than the other non-ionic resins (set forth in more detail with respect to the next required non-ionic step below) when contacted with the elution liquid so that they can be regenerated more completely than the other non-ionic resins of the next required step. As such, it is preferable to include this optional step. The major distinction between the resin used in this optional step and the non-polyacrylate, the non-polymethacrylate, and the non-polyacrylate/methacrylate non-ionic resins in the subsequent required step is one of size exclusion and swelling on exposure to elution fluid. The resin of the present step has a larger effective size and is typically >about 0.30 mm minimum effective size, preferably ≧about 0.35 mm minimum effective size (as that term is used in Itochu's product literature); while the non-polyacrylate, non-polymethacrylate, and non-polyacrylate/methacrylate non-ionic resins used in the subsequent required step is smaller, typically ≦0.30 mm, preferably ≦about 0.25 mm. Other non-ionic polymeric materials are suitable for this optional step provided that they have similar size exclusion and elution swelling properties.

As mentioned, in addition to removing some non-steroidal components, this optional step also removes a portion of certain steroids. In applications where the particular steroids being removed with the impurities are not of concern, if there is only a slight impact on the yield of the steroids that are intended to be recovered, the non-ionic resin laden with the impurities and such steroids may simply be discarded or regenerated for reuse without recovery of the compounds extracted by such resin. Alternatively, if one or more of the desired steroid compounds are significantly removed by this step or one or more of the removed impurities are of commercial value, the spent resin can be separated from the urine, the extracted compounds eluted therefrom, and the eluted compounds further processed for separation, purification, and recovery. In the case where urine from pregnant mares urine is used, significant amounts of the equilin/estrone content of the inflow material are removed by this step and recovery thereof is generally sought. Because a number of the non-steroidal impurities are removed in this step, the subsequent resin extractions are more efficient and the subsequent resins need not be regenerated as often. While this means that the resin used in this step may have to be replaced and/or regenerated more often than the others, because of the greater swelling and release of extracted materials when subjected to elution fluid, the resins used here are easier to regenerate resulting in a net savings in the overall economies of the process.

Once (a) the phenolic content has been sufficiently reduced and (b) non-steroidal impurities have optionally been reduced by the optional non-ionic resin extraction step above, the reduced-phenolic content urine (the fourth liquid remainder or the first liquid remainder, respectively, as appropriate) is now ready for the actual desired steroid, preferably estrogenic steroid, more preferably conjugated estrogen constituent, extraction procedures. The fourth or first liquid remainder is now contacted with a resin capable of adsorbing the first group of esterified steroid constituents (first ESC) of the fourth or first liquid remainder while not substantially absorbing the second group of esterified steroid constituents (second ESC) of the fourth or first liquid remainder. The first ESC of the fourth or first liquid remainder, when pregnant mare's urine is used as the urine source, comprises the conjugated forms (i.e., the sodium salts of the sulfate esters) of estrone and equilin with smaller amounts of 17α-estradiol, 17α-dihydroequilin, 17α-dihydroequilenin, and 17β-dihydroequilenin. Examples of resins that can absorb the first ESC and do not substantially adsorb the second ESC include non-ionic resins including, but not limited to, those non-ionic macroporous resins having backbones selected from the group consisting of polystyrene-divinylbenzene, poly(meth)acrylates, and polyphenolics. The poly(meth)acrylates are the same as those set forth in the optional step above; and while these resins can be used in this step alone without the above optional step or in conjunction with the optional step above using the same or same class of resins as in the optional step above, they are less desirable in this step because the other resins (the non poly(meth)acrylates) for this step are more efficient.

One particularly preferred polystyrene-divinylbenzene resin for this required step that is commercially available is Diaion® HP20 having pore volume of 1.3 ml/g, a surface area of 600 $m^2$/g, an average pore radius of 260 Å; and a minimum effective size of about 0.25 mm (available from Itochu). Other non-limiting exemplary Itochu non-ionic resins suitable for use at this step include Diaion HP20, HP21, SP825, SP850, SP70, SP700, HP20SS, and SP20SS. Particularly preferred commercially available polyphenolic resins include, without limitation: Duolite XAD-761 (available from Rohn and Haas) and Amberline XAD 761 (available from Rohm and Haas). Other polymeric backbones for use as alternatives to the foregoing will be well known to those of ordinary skill. These required step non-ionic resins absorb the first ESC with a high degree of efficiency while the second ESC barely or only slightly interact with the resin at all. To be sure that the resin is working appropriately, the effluent is monitored (preferably by HPLC) for one or more of the first ESC components. At first, there should be no first ESC as it should all have been absorbed. If there is first ESC content in the effluent, the resin might be loaded and needs to be changed or the contact time with the resin needs to be increased. After some amount of time, the effluent will begin to show signs of increasing first ESC which means that the resin has reached its capacity and needs to be replaced. The effluent showing first ESC may be recycled to another portion of resin in order to capture the first ESC content thereof. As estrone, equiline, and 17α-dihydroequilin are the predominantly extracted materials by these resins, monitoring the input and outflow for one of these is generally more desirable, but monitoring of other constituents that should be extracted by these resins is also possible as desired. The flow rate, temperature, and monitoring times are generally (and preferably are) the same as set forth above with respect to the phenolic reduction step, but need not be so and may be adjusted as desired.

Once it is determined that the nonionic resin needs to be replaced and/or regenerated, the nonionic resins, whether in this required step or in the previous optional step are taken off-line and first contacted with purified water and then eluted it with a water miscible solvent as discussed more fully below. The elution media is continued to be used until it no longer elutes any steroidal materials of interest from the resin. These eluates are collected and stored for further purification and processing as set forth more fully below. In the meantime, these resins are regenerated as set forth below.

The urine effluent which has been reduced in first ESC (hereinafter the "second liquid remainder") is then contacted with a different resin capable of extracting the second ESC therefrom. This resin is generally a weakly cationic exchange resin. For purposes of the present invention, "weakly cationic exchange" with respect to the resins, refers to the resin's character when added to pH 8.5 water (generally an aqueous 2% sodium sulfite solution). Suitable weakly cationic exchange resins include, but are not limited to, those having a backbone selected from polystyrene-divinylbenzene, poly (meth)acrylics, and polyphenolics with weakly cationic exchanging side groups. The weakly cationic exchanging side groups are anionic in nature having a negative charge when ionized and may include, without being limited to, sulfate, sulfonate, carboxy, and phosphate.

A particularly preferred resin for this step is a weakly cationic exchange resin of a polystyrene-divinylbenzene backbone having sulfate groups, and an especially preferred resin of this type is commercially available under the name RELITE™ EXL 04 (available from Mitsubishi). Other such cationic exchange resins for use in the invention in this step include, without limitation, the following resins available from Itochu: Diaion PK208, PK212, PK216, PK220, PK228, UPK228, SK1B, SK1BH, SK104, SK110, SK112, SK116, RCP21H, RCP23H, RCP160M, RC01H, RC02H, RCP11H, RCP12H, RCP13H, UBK510L, UBK530, UBK535L, UBK550, UBK555, HPK25, PK208, PK212, PK216, PK220, PK228, UPK228, and Relite EXC04 (each having a polystyrene backbone and a sulfate pendant group); Prepex SP (having 3-sulfatopropyl pendent groups); Diaion CR11 (having a polystyrene backbone and N,N-di(sodiumcarboxymethyl) aminomethyl pendent groups); CRP200 (having a polystyrene backbone and phosphatomethyl pendent groups); Diaion WK10, WK10S, WK 11, WK100, WT 01S (being polymethacrylic acid); Diaion WK40 (being polyacrylic acid); etc. Other similar resins from other manufacturers will be apparent to those of ordinary skill in the art.

The effluent or liquid in contact with the weakly cationic exchange resin is monitored for second ESC content. Initially, the second ESC content of the effluent should be zero and detection of second ESC in the effluent indicates that the contact time with the resin is insufficient, either because the flow rate is too high, or because the resin is spent or fully loaded. In such a case, (a) the flow rate should be adjusted and/or (b) the resin in use should be regenerated or replaced with fresh resin and (c) the effluent containing second ESC should be recycled to additional resin for capture of the effluent second ESC. The flow rate, temperature, and monitoring times are generally (and preferably are) the same as set forth above with respect to the phenolic reduction step and the required first ESC reduction step, but need not be so and may be adjusted as desired. The effluent of this step (the "third liquid remainder") can be further processed for recovery of steroids that have not been recovered in prior steps; however, it is generally devoid of steroids and usually simply discarded.

Once it is determined that the weakly cationic exchange resin needs to be replaced or regenerated, it is taken off-line and first washed with purified water, then eluted with a basified water-miscible solvent-aqueous solution as discussed more fully below. The elution media is continued to be used until it no longer elutes any steroidal materials of interest from the resin. The resin is then regenerated as set forth below.

The non-ionic resin laden with the first ESC and the weakly cationic exchange resin laden with the second ESC are separately eluted by independent parallel procedures. (The non-ionic resin from the optional impurity reduction step may also be eluted and after separation of some, preferably all, of the impurities, the effluent thereof can be similarly processed as discussed herein if desired.) Each of the esterified steroid laden resins are eluted by an elution fluid that has at least a water-miscible organic solvent, optionally (and preferably) in admixture with water. The water-miscible organic solvent is preferably selected from the group consisting of water-miscible ethers, lower aliphatic alcohols, lower aliphatic ketones, and mixtures thereof. For purposes of the water-miscible organic solvents, "lower aliphatic" means straight or branched chain as well as cyclic aliphatic groups having up to 6 carbons; straight and branched chains preferably have up to 4 carbons, more preferably are methyl, ethyl, propyl or isopropyl, still more preferably methyl, ethyl or isopropyl. Exemplary cycloaliphatic groups are preferably cyclopentane or cyclohexane. Suitable elution ethers include water miscible cyclic ethers such as tetrahydrofuran and dioxane, etc. Suitable elution open chain ethers include ethylene glycol dimethyl ether (=monoglyme), diethylene glycol dimethyl ether (=diglyme), ethyloxyethyloxy ethanol (=Carbitol). Suitable elution alcohols include methanol, ethanol, propanol, isopropanol, as well as the corresponding alcohols containing 5 or 6 or 7 carbon atoms, although methanol, ethanol, and isopropanol are preferred, while methanol is most highly preferred. Elution ketones have 1-5 carbon atoms in each aliphatic group, with acetone being the most highly preferred.

In addition, the elution fluid for the weakly anionic exchange resin may contain an acidifier, preferably an inorganic acidifying agent such as hydrohalic acid (such as hydrochloric acid or hydrobromic acid, etc); sulfuric acid, phosphoric acid, nitric acid, etc, with sulfuric acid being highly preferred. A most highly preferred acidified elution fluid for the weakly anionic exchange resin is a solution of a lower alkanol in 2% w/v aqueous sulfuric acid, most preferably a 50/50 v/v solution of methanol in 2% w/v aqueous sulfuric acid.

Also, the elution fluid for the weakly cationic exchange resin may contain an alkalinizing agent, preferably an inorganic alkalinizing agent such as alkali metal (preferably sodium or potassium) or alkaline earth metal hydroxide although any alkalinizer that does not react with the esterified steroids, that can provide the requisite pH, and can be removed later in the process is suitable. The aqueous effluent fluid having an alkalinzer present preferably has a pH in the range of from neutral up to pH of 13, preferably a pH of about 10 to about 12. The ratio of water-miscible organic solvent to water (or alkalinized water) is generally in the range of 30:70 vol/vol to 60:40 vol/vol, more preferably about 50:50 vol/vol. As suitable elution fluid for the weakly cationic exchange resin, a mixture, 50 parts by volume of 4% sodium hydroxide and 50 parts by volume of an alcohol where the alcohol is selected from either methanol or isopropanol or a mixture thereof is used. A highly preferred elution fluid for the weakly cationic exchange resin is a 50:50 v/v mixture of methanol and a 2% w/v aqueous solution of sodium sulfite.

During elution of the respective resins, the temperature is desirably maintained at about 10° C. to about 20° C., preferably about 12° C. Typically, about 3 to about 10, preferably about 5 to about 7 column volumes of elution fluid are used to elute the respective esterified steroids from the respective resins. A flow rate of about 0.568 liter/min to about 2.839 l/min (about 0.15 to 0.75 gal/min), preferably about 0.946 l/min (about 0.25 gal/min) through a typical 6 inch by 8 foot column is generally preferred. The elution fluid generally swells the resin to increase the pore size and release the trapped materials.

As desired, the eluate from each resin loaded with esterified steroid may be collected in a single container for each column being eluted or in multiple fractions of each. Preferably, eluate is collected in 10 ml fractions with each sample being separately labeled. Smaller or larger fractions may be used as desired without departing from the present invention. In either case, the quantitative composition of each eluate or eluate fraction is optionally determined in any suitable manner known in the art, preferably by HPLC. Once eluted, the eluates containing the first ESC or the second ESC, respectively, or subsets thereof (and optionally those containing other steroids) can be either further processed immediately or stored for processing at a future time. If stored, it is preferable to store the eluates at temperatures of about 1° C. to about 10° C., preferably at about 3° C. to about 7° C., most preferably at about 5° C. so as to keep esterified steroid degradation to a minimum. The various isolated mixed esterified steroids in the effluent fluids are stable for at least 3 years when stored at the recommended temperature. Storage at higher temperatures is possible, but stability over time in storage drops considerably with increasing temperature. After elution of the esterified steroids from the resins, the resins can be regenerated for use.

The anion exchange resins (used in the phenolic reduction step) are typically regenerated by passing about 5 to about 7 column volumes of purified water (pH about 7) therethrough to rinse off most undesired water soluble components, then passing about 7 to about 9 column volumes of a 50:50 (v/v) methanol water solution containing 2% w/v $H_2SO_4$ therein through the column to elute the entrapped materials, and then 5-7 column volumes of purified water are used to wash the bed free of the acid solution. The non-ionic resins are typically regenerated by passing about 5 to about 7 column volumes of purified water (pH about 7) therethrough to rinse the resin free of undesired materials, then passing about 7 to about 9 column volumes of methanol through the column to elute the desired entrapped materials, and then 5-7 column volumes of purified water are used to wash the bed free of the methanol. The cationic exchange resins are typically regenerated by passing about 5 to about 7 column volumes of purified water (pH about 7) therethrough to rinse the resin free of undesired materials, then passing about 7 to about 9 column volumes of a 50:50 (v/v) methanol water solution containing 2% w/v $Na_2SO_3$ therein through the column to elute the entrapped materials, and then 5-7 column volumes of purified water are used to wash the bed free of the sulfite solution. Alternate regeneration schemes will be known to those of ordinary skill in the art. The resins so regenerated can then be used as fresh resin in the appropriate steps above.

It should be noted that in all of the above discussion of columns, those of ordinary skill in the art will be able to modify the same for suitable use with respect to beds or to other types of containers for contacting the resin with the fluids in question, whether such are continuous or static (batch) type setups, and such variations are within the scope of the present invention.

The collection of elution samples and the information about the steroid content of each sample provides an eluate database that allows for recombination of various sample fractions to meet a pre-determined constituent content and concentration profile. In the case of preparing a generic version of a conjugated estrogen product, multiple samples of different lots of such product are analyzed for the conjugated estrogen constituent profile and concentration ranges of each constituent so as to create an "existing product profile". Since the prior product may vary from batch to batch, those components that are always present in the prior product are required to be present in any generic equivalent, while those that are only present sometimes may be present, but are not required to be present in any generic equivalent thereof. In addition, the required components need only be present within the concentration ranges seen in any existing product sample, while the optional components may be absent, or present at or below the amounts seen with any existing product sample. As such, with the knowledge of the existing product profile, the elution samples in the eluate database can be recombined in varying proportions to obtain a combination product that has all of the required components in the appropriate concentrations and all, some, or none of the optional components at levels at or below those seen with any sample of the existing product. Once establishing the "existing product profile", such profile may be fixed as a consistent reference standard and the elution samples may be consistently recombined from batch to batch to arrive at a consistent generic version of the existing product (or at least a more consistent version of the previously existing product). Alternatively, the number of "optional components" can be arbitrarily limited to less than all of those seen in the existing product and the concentration ranges permitted for the generic version can be arbitrarily limited to the common concentration ranges seen in the existing product on a component-by-component basis. In these last variations, the generic version made possible by the present invention is actually a more consistent material, with fewer "extraneous steroids" than the existing PREMARIN product. The recombined eluates may also be concentrated or further purified, especially in obtaining a product suitable for incorporation into oral and other dosage forms. Alternatively, the eluates may be combined as is to obtain a product having an appropriate profile and the result introduced into a suitable dosage form, as is or after the reduction thereof to powder.

If desired, additional resin extractions can be inserted at any point once the phenolics have been reduced and before or after the eluates have been reduced to powder. For example, an eluate may be contacted with another resin to either purify the steroid components or to separate them from one another to a greater degree or an eluate may be reduced to powder in known manners, most preferably by spray drying, then taken up in a suitable solvent and then contacted with further resins so as to further separate or purify the materials. Other variations on the theme will be apparent to those of ordinary skill.

Notwithstanding the above, it is preferable to further purify and concentrate the steroids in the respective eluates before recombining them. The following procedures can be applied to either the recombined eluates containing the steroids, or to individual eluate samples which can be recombined at any stage along the process, but preferably are recombined after the steroids in each sample have been reduced to a purified powder material (which powder material may be either a single compound or a mixture of compounds). For convenience, the following will be described with respect to any one eluate sample, but it is applicable to all eluates from the non-ionic resin extraction steps and the weakly cationic exchange resin extraction step whether run on different eluates simultaneously, sequentially, or on combinations of eluates. The following process may also be used on samples containing non-esterified steroids for additional recovery of such steroids (for conversion to esterified steroids or for use for other purposes) which may be recovered at other points in the process as well.

The further purification steps will be discussed with reference to eluates obtained from pregnant mare's urine containing conjugated estrogen constituents, but the processes described are equally applicable to eluates obtained form urine of other sources that have esterified steroids, whether or not conjugated estrogen constituents.

In a first alternative purification procedure, the solvents in the eluates are removed (typically subjected to vacuum evaporation of the solvent using a vacuum pressure of generally under 100 mm Hg, preferably not more than about 10 mm Hg and at a temperature of generally not exceeding 40° C. A suitable apparatus is a Rota-vap. If desired, other drying techniques that do not substantial negatively impact the desired steroids may be used and are well known in the art. The eluate (first solution) is concentrated until a very viscous, dark residue (first residue) is obtained. The residue is removed and a lower aliphatic ketone (having 1-5 carbons in each alkyl group), preferably acetone, is added resulting in a second solution and a second residue. Generally about 0.5 to about 1.0 L, preferably about 0.75 L of ketone is used (in fractions) for the first residue resulting from one 10 ml eluate. The ketone is added at a temperature of about 20° C. to about 40° C., preferably about 30° C. The conjugated estrogen constituents (generally along with other esterified steroid constituents present) are taken up by the ketone from the first residue which can be observed by a color uptake by the ketone. The ketone laden with the steroid constituents is then separated from the second residue by conventional techniques. Multiple fractions of this extraction of the steroidal constituents by the ketone may be combined and then filtered (preferably through diatomaceous earth) or separately filtered and then combined, or simply filtered without combining them. The second residue, remaining on the filter, may be discarded. The filtrates are then reduced in volume (typically under vacuum under the substantially same set of conditions of temperature and pressure and equipment as set forth above concerning the eluates) until a heavy black mass remains (third residue). The heavy black mass is removed from the volume reduction conditions and water is added to dissolve the mass to give a third solution. A neutral salt (preferably sodium chloride) is added until saturation (to give a fourth solution), followed by the addition of n-butanol or isobutanol (at about room temperature, i.e., about 18° to about 25° C.). A number of extractions with n-butanol or isobutanol is carried out until no additional product extraction is evident. The butanol layer (fifth solution) is separated from the aqueous phase and the butanol is removed therefrom to dryness (typically by evaporation generally under the same conditions of temperature, pressure and equipment as set forth above concerning the eluates) to produce a dark brown powder (first powder).

The first powder (which is hygroscopic) is then optionally washed with a warm non-reactive organic solvent such as warm toluene or warm hexane (typically about 500 ml of solvent at about 25° C. to about 45° C., preferably about 35° C.), which removes free steroids and some apparent degradation products (sixth solution) from the first powder, leaving behind a fourth residue) (such as an HPLC peak appearing at about 39 minutes (in the method in which the mobile phase gradient from water to acetonitrile (each with about 0.1% trifluoroacetic acid) is completed in a little over 4 hours). The fourth residue remaining is separated from the sixth solution and then dissolved in warm acetonitrile (generally about 200 ml to about 500 ml, preferably about 300 ml at about 20° C. to about 40° C., preferably about 30° C.) and the resulting solution (seventh solution) is stored at about 1° C. to about 10° C., preferably about 3° C. to about 5° C. for a period of about 24 to about 36 hours. The solutions are then dried, generally by evaporation or spray drying, to result in a dry first product, which is crystals or powder, depending upon the manner of drying it.

In a second alternative purification process, the solvents in the elutes (first solutions) are removed as in the first purification alternative above. In this second alternative, spray drying is preferably used however, to give rise to a second powder. To the second powder material, a dry $C_{1-3}$ lower alkanol, preferably methanol, ethanol, propanol, or isopropanol, more preferably methanol, is added to result in an eighth solution of some of the steroidal components, while other steroidal components remain undissolved (fifth residue). The eighth solution and the fifth residue are separated in conventional manners and each is further processed separately.

The fifth residue (which was not dissolved by the $C_{1-3}$ lower alkanol in the second purification alternative above) is dried of any residual $C_{1-3}$ lower alkanol. A $C_{1-5}$ lower aliphatic ketone, preferably acetone is added to dissolve desired steroids therein (ninth solution), while any undissolved material (sixth residue) can be discarded. The ketone is then removed from the ninth solution (generally by vacuum evaporation, generally under the same conditions discussed above concerning the vacuum evaporation of the eluate solutions). The dried residue (seventh residue) from the ketone removal is washed with non-polar, non-reactive, organic solvent preferably toluene or hexane, more preferably toluene to give an eight resikdue and a tenth solution. The tenth solution is separated from the eighth residue and a butanol is added to dissolve desired components. The butanol solution (eleventh solution) is separated from the solid remainder (ninth residue) and the butanol is then removed form the eleventh solution to give a solid desired second product; the material which did not dissolve in the butanol (ninth residue) is discarded.

The lower alkanol is removed from the eighth solution (generally by vacuum evaporation and generally under the same conditions and procedures asset forth above concerning the eluate solution) to give a tenth residue, which is then washed with a non-reactive non-polar organic solvent, preferably toluene or hexane, more preferably toluene to result in a twelvth solution and an eleventh residue. The non-reactive organic solvent removes free steroids, while the esterified steroids generally remain undissolved in the wash solvent. The twelvth solution and eleventh residue are separated. Any residual non-reactive solvent is removed from the eleventh residue and a butanol, preferably n-butanol or isobutanol, more preferably n-butanol is added to dissolve the desired steroid sulfate esters resulting in a thirteenth solution and a twelvth residue. The butanol solution (thirteenth solution) is separated from the twelvth residue and then the butanol is removed from the thirteenth solution (typically by vacuum evaporation under the same conditions as set forth above concerning the eluate vacuum evaporation) to result in a desired product (dry third product).

The steroidal content and concentrations of the resulting desired products (the solid products remaining after removal of the butanol from the butanol solutions thereof) is optionally analyzed, and the resulting powder is labeled and stored for recombining with other steroid samples (if not previously done) to meet a pre-determined product constituent and concentration profile.

In the meantime, optionally, the free steroids present in the non-reactive organic solvent solutions described above (and in parallel fashion any free steroids obtained from the conversion of solid esterified steroids (found in the non-reactive, non-polar solvent discussed above, i.e., the sixth, tenth, and/or twelvth solutions above) are concentrated (generally by use of a Rota-vap) to yield a concentrated fourteenth solution. An ether solvent, preferably in diethyl ether, is then added whereby organic impurities are left as solids (thirteenth residue) while the free steroids dissolve (fifteenth solution). The fifteenth solution is separated from the thirteenth residue by known techniques, preferably filtration. The separated fifteenth solution is concentrated and dried by known techniques and the residue (fourteenth residue) is dissolved in a solvent such as pyridine to give a sixteenth solution containing free steroids. The pyridine solution of the free steroids, if desired, is then optionally sulfated to yield further purified esterified steroids.

Each batch of purified esterified steroid (whether the originally present conjugated estrogen constituents or those optionally derived from the conversion of the esterified steroids or the free steroids) is analyzed for the type of esterified steroid present and its concentration, and such information is stored in a database. (If a similar analysis was done at an earlier stage, this analysis step may not be required here, but preferably it is done at this point.) Preferably, the analysis at this point is by gas chromatography.

Compilation of the qualitative and quantitative information on esterified steroid content of multiple samples in a database allows for the recombination of appropriate amounts of different purification samples so as to arrive at a recombined product that is extremely reproducible and meets virtually any pre-defined product profile. Such recombinations can be made in any desired manner; however, it is preferable to dissolve the appropriate amounts of the different samples in a lower alkanol, preferably ethanol, either by blending the solids and dissolving the blend or by dissolving the specific solids and then blending the solutions, or a combination of both. The blended solution is then dried, preferably by spray drying.

The pre-determined steroid product profile may be any standard that one wishes to establish. In one aspect of the present invention the pre-determined product profile is in accord with the requirements of one of USP23, USP 24, USP25, USP26 or USP27. In another aspect of the present invention, the pre-determined product profile is in accord with the requirements of the FDA Guidance for Industry Conjugated Estrogens, USP-LC, MS Method for Quantitative Characterization and Documentation of Qualitative Pharmaceutical Equivalence, dated March 2000 ("FDA Guidance"). In a third aspect of the present invention, the pre-determined product profile is derived from gas and liquid chromatography results performed on one or more samples of PREMARIN conjugated estrogens. Other authoritative recitations of product steroid content and concentration, such as the various national or regional pharmacopoeias may also form the basis of a product profile set as the arbitrary profile to meet. In addition, it is also suitable to select an arbitrary profile which is not designed to meet equivalency standards to another product and still be within the scope of the present invention.

In accordance with another aspect of the invention, when the main emphasis is obtaining conjugated estrogens, it is preferable to use a pregnant mare as the urine source (although other urine sources can still be used). Sub-batches of the first ESC and second ESC are prepared as described above from different urine specimens each harvested during the gestation period of the mare in question. Each sub-batch is analyzed for the individual compounds using conventional techniques, and the data is stored (as a database or spreadsheet). From the analysis of the collective data, a blending procedure is performed to produce a mixed conjugated estrogen which meets one or more of the above pre-determined product profiles or another pre-determined product profile.

The esterified steroids obtained by the present invention can be formulated as therapeutic products either alone or in combination with other steroids and/or still other active agents for use in estrogen replacement therapy or hormone replacement therapy or for any steroid use that the particular steroid content is suitable for. Such uses are well known in the art. When used as combination products, the other active agents may be incorporated within the same dosage form or may be in a separate dosage form (for either simultaneous or sequential administration). In addition, they may be chemically modified to other active agents, in particular to other agents having the steroidal tetracyclic structure, especially when they have been purified to single compounds.

Conjugated estrogen tablets can be prepared in any manner known in the art, for example (without limitation), as set forth in U.S. Pat. No. 5,908,638 (incorporated by reference herein). Combination products with other active agents can be prepared, for example (without limitation) in accordance with US Published Application 2001/0034340 (incorporated herein by reference). Other steroid containing dosage forms can be prepared analogously thereto. The tablets may include a wide variety of inactive ingredients including carriers and adjuvants, a small, non-limiting sample of which includes: starch, lactose, dicalcium phosphate, microcrystalline cellulose, sucrose, kaolin, water, polyethylene glycols, non-ionic surfactants, edible oils (such as corn, peanut, sesame, canola, olive), flavoring agents, coloring agents, preservatives and antioxidants (such as for example vitamin E, ascorbic acid, BHT, and BHA), tableting lubricants, tableting disintegrants, flow agents, enteric coating materials, time-delay coating materials, etc. The steroids obtained by the present invention may be incorporated into granules, spheroids or other multiparticulate forms. The formulations can be tableted or incorporated into gelatin capsules, lozenges, transdermal devices, creams or lotions or ointments, or formulated as injectable solutions, suspensions or lyophilizations for reconstitution. Oral dosage forms are preferred, but any suitable dosage form that will deliver the steroid to the patient is suitable and many different suitable dosage forms are known in the art.

Dosages of individual steroids as well as mixed conjugated estrogens are well established for a variety of conditions as those of ordinary skill in the art would be well aware.

EXAMPLES

The following examples exemplify, but do not limit, the present invention.

Example 1

Overall Evaluation of Pregnant Mare's Urine (PMU)

Three samples of PMU are collected and analyzed using conventional techniques. Table I summarizes the results of the analysis.

TABLE I

|  | Sample 1 | Sample 2 | Sample 3 |
|---|---|---|---|
| pH | 8.2 | 8.5 | 8.1 |
| Estrogens wt % by dry wt | 7.4 | 7.7 | 7.5 |
| Sulfate Content[1] | 0.257 (70.54) | 0.294 (77.68) | 0.302 (79.79) |
| Cresol Content[1] | 0.80 (211.35) | 0.79 (208.72) | 0.85 (224.57) |
| HpMF[1,2] | 0.262 (68.96) | 0.266 (70.28) | 0.271 (71.58) |

[1]Expressed g/gal with mg/L in parentheses
[2]HpMF is dihydro-3,4-bis(3-hydroxyphenyl)methyl-2,(3H)-furanone It can be observed from Table I that the approximate yield of estrogens from PMU is in the range of 7.4-7.7% of the dry weight of the urine. The 0.257 to 0.302 g/gallon (70.54 to 70.79 mg/L) of sulfates is the amount of sodium sulfate resulting from the release of the sulfate group from all sulfated species in the urine, whether estrogens other steroids, or non-steroidal entities.

Example 2

Stability of the Raw PMU

PMU samples are collected and stored over a period of 5 months and analyzed by HPLC. Samples are stored at 2° C. One sample is stressed by exposure to 50° C. for four days. Two wavelengths (215 nm and 235 nm) are used for detection and the components of the samples are separated by a gradient method with using 0.1% trifluoroacetic acid in acetonitrile and 0.1% trifluoroacetic acid in water as the mobile phases (where the starting ratio of the water solution to the acetonitrile solution is 90:10 and the ending ratio is 10:90) on a Phenomenex ODS-3 250 mm/4.6 mm column with a 5 μm column.

The peaks are observed up to about 48 minutes in the chromatograms are due to phenolic constituents and blood proteins. Differences observed in this portion of the chromatograms are due differing portions of these extraneous components. They are believed to, differ from lot to lot of PMU due to varying feedstocks of the animals and varying collection time points within the gestation period. Conjugated estrogens elute from this procedure at approximately 49-55 minutes. A comparison of the unstressed samples and the sample stressed by exposure to 50° C. for 4 days will show substantial reduction (if not complete elimination of the peaks associated with conjugated estrogens and the appearance of or substantially higher concentrations of unconjugated estrogens. A substantial drop in the amount of phenolic constituents in solution will also be observed from samples exposed to the stress conditions, which is attributed to the fact that under the stress conditions, many of the phenolic constituents will precipitate.

Example 3

Preparation of the Urine when pH Adjustment Used

The initial pH in some samples of PMU may be found to vary from pHs at which the conjugated estrogens are stable. In such-samples pH adjustment is desired. In this Example, pH of PMU initially determined to be between 5.5-8.5 is adjusted to a pH of 8.5 to 9.5 by monitoring the pH of the urine in a urine tank with a pH meter probe inserted into the tank. The probe is also used to stir the urine in the tank. 6 M NaOH is then added in aliquots while monitoring the pH of the urine until a pH of 8.5-9.5 is obtained.

A positive displacement pump is used to pump the pH adjusted urine through a basket filter (5 μm pore size) to remove large particulate matter. The residue is discarded and the liquid filtrate is pumped through a filter press (1 μm pore size filter element coated with Celite diatomaceous earth). The flow rate through the filter is approximately 0.5 to 2.0 gallons/minute. The filtrate is then passed through a third filter of approximately 0.1 μm pore size to remove yet finer particulate matter and the end filtrate is collected in a holding tank.

Example 4

Extraction of Phenolic Constituents from the Filtered, pH Adjusted Urine

A positive displacement pump is then used to pump the filtered result of Example 3 through a glass column (6 inch (15.24 cm)×8 feet (2.44 m)) that is packed with Dowex XAD 2 weakly anionic exchange resin (a polystyrene-divinylbenzene polymer backbone that is 12% cross-linked) maintained in the free acid form. This resin removes the phenolic contaminants that would otherwise interfere in the efficient extraction of the estrogenic materials in the subsequent steps. Efficiency of the phenolic content reduction is monitore by off-line HPLC determinations conducted approximately every three hours by an analysis of a sample of the column effluent.

After processing approximately 1000 gallons (3785 L) of fluid, the column is regenerated by first taking the column off-line and passing 5-7 column volumes of purified water (pH adjusted to about 7) through the column. Then 7-9 column volumes of 4% caustic solution are applied to the column to desorb the phenolics from the the column. This solution containing the desorbed phenolics is typically discarded, but may be processed for recovery of the phenolic materials for other uses. Then, 5-7 column volumes of purified water are applied to the column to wash the column free of residual caustic solution, after which the column is placed back in the free acid form and is ready for reuse.

Example 5

Inherent Steroidal Extraction Ability of Certain Resins

Exemplary nonionic resins Diaion HP20 and SP207 and exemplary weakly cationic exchange resin Relite EXC 04 are individually packed into columns 2 inches wide and 24 inches long. A separate 10 gallon (37.85 liter) sample of pregnant mare's urine (each of which has previously been reduced in phenolic constituents) is passed through one of the preprared columns at a flow rate of 0.25 gallons per minute. A different 10 gallon sample of phenolic reduced pregnant mare's urine is used for each each column as well as for each run of each column. After the urine has completed percolating through the columns. Each column is washed with water and then eluted. The non-ionic columns (HP20 and SP 207) are eluted with methanol. The weakly cationic exchange resin (Relite) is eluted with a 50:50 v/v solution of methanol and 2% w/v aqueous sodium sulfite. Each eluate is analyzed for its steroid content by gas chromatography. The label claim, the total of 10 specific steroids as a % of label claim, and the proportions of each of the specific 10 steroids to each other are shown in the Table below. The label claim in this table is the amount on a percent w/w basis that the total of the 10 specifically listed steroids represents out of the total amount of materials extracted by the resins.

TABLE 2

| | HP20 | SP207 | Relite |
|---|---|---|---|
| Total of 10 steroids[1] | 8.932[A]<br>10.088[B]<br>8.867[C] | 7.024[A]<br>1.058[B] | 1.719 |
| Proportions | | | |
| 17α-estradiol | 4.133 (0.369)[A]<br>0[B]<br>0[C] | 0[A]<br>0[B] | 0 |
| 17α-dihydroequilin | 17.424 (1.556)[A]<br>16.814 (1.696)[B]<br>26.392 (2.340)[C] | 38.541 (2.707)[A]<br>39.588 (0.419)[B] | 1.512 (0.026) |
| 17β-dihydroequilin | 1.458 (0.130)[A]<br>1.363 (0.137)[B]<br>3.521 (0.312)[C] | 4.306 (0.302)[A]<br>11.460 (0.121)[B] | 5.986 (0.103) |
| Estrone | 34.069 (3.043)[A]<br>36.806 (3.713)[B]<br>32.637 (2.894)[C] | 24.710 (1.756)[A]<br>19.467 (0.206)[B] | 35.031 (0.602) |
| Equilin | 42.916 (3.833)[A]<br>45.017 (4.541)[B]<br>37.451 (3.321)[C] | 32.443 (2.279)[A]<br>29.485 (0.312)[B] | 57.471 (0.988) |
| 17β-estradiol | 0[A]<br>0[B]<br>2.537 (0.225)[C] | 3.352 (0.235)[A]<br>8.707 (0.092)[B] | 12.913 (0.222) |
| 17α-dihydroequilenin | 1.927 (0.172)[A]<br>2.016 (0.203)[B]<br>2.695 (0239)[C] | 4.288 (0.301)[A]<br>14.047 (0.149)[B] | 0.654 (0.011) |
| 17β-dihydroequilenin | 0.684 (0.061)[A]<br>0.067 (0.061)[B]<br>0.852 (0.076)[C] | 1.021 (0.072)[A]<br>0[B] | 0.803 (0.014) |
| Δ$^{8,9}$-dihydroestrone | 8.115 (0.725)[A]<br>11.471 (1.157)[B]<br>8.968 (0.795)[C] | 10.996 (0.772)[A]<br>29.493 (0.312)[B] | 34.107 (0.586) |
| Equilenin | 2.871 (0.256)[A]<br>3.394 (0.342)[B]<br>2.593 (0.230)[C] | 1.848 (0.130)[A]<br>0[B] | 5.164 (0.089) |

[1]Total extract of the following 10 steroids as a % of the total material extracted
[A]First run of multiple runs - % of total of the 10 steroids, % of the label claim in parentheses
[B]Second run of multiple runs - % of total of the 10 steroids; % of the label claim in parentheses
[C]Third run of multiple runs - % of total of the 10 steroids, % of the label claim in parentheses Example 6

Extraction of Estrone and Equiline (PMU Major Estrogen Constituents)

The phenolic reduced liquid result of Example 4 is then pumped through a Diaion HP20 (a macroporous polystyrene-divinylbenzene completely non-ionic resin available from Itochu) packed glass column (6 inches (15.24 cm)×8 feet (2.44 m)). This resin extracts the estrone and equiline (the two major peaks of estrogens present in PMU) with a high degree of efficiency. The efficiency of the removal of these components is monitored off-line by HPLC analysis of samples of effluent of the column at approximately three hour intervals. When the column is no longer adequately removing estrone and equiline, or at any other time that elution of the resin is desired, the column is taken off-line and the extracted steroids are eluted therefrom by contacting the column with an elution fluid having about 2% NaOH in a water:methanol 1:1 solution. The 2% water in aqueous methanol solution is continued to be applied until the effluent stream thereof contains no further estrone or equiline (as determined by off-line HPLC testing of samples of such effluent). The on-line effluent that is reduced in estrone and equiline is directed to another resin (detailed in Example 7) for extraction of further steroids not yet extracted from the fluid effluent of the present step.

Example 7

Extraction of PMU Minor Estrogen Constituents

The on-line effluent from Example 6 is then pumped through a RELITE EXL 04 (a weak cationic exchange resin having a polystyrene-divinylbenzene backbone with sulfate pendant groups available from Itochu) packed glass column (6 inches (15.24 cm)×8 feet (2.44 m)) to extract the remaining minor steroid constituents still contained in the on line effluent from Example 6. The efficiency of the extraction is monitored by off-line testing of samples of the effluent from the RELITE EXL column. Once these minor estrogen constituents begin to appear again or appear to increase in the effluent, the RELITE EXL is taken off-line and eluted with a 2% NaOH in water:methanol (1:1) solution. The column is continued to be contacted with the elution fluid until the elution fluid shows substantial drop in the minor estrogen constituents.

Example 8

Alternate Extraction of Estrone and Equiline

In an alternative situation, an additional column is introduced between the result of Example 4 (the phenolic reduction) and the beginning of Example 65 (the main estrone and equiline extraction). In this Example, the phenolic reduced result of Example 4 is applied to a 6 inch (15.24 cm)×8 ft (2.44 m) column of HP2MG (a non-ionic polymethacrylate resin available from Itochu). Efficiency of the extraction is monitored off-line by testing of samples of the effluent of this step for the presence of estrone and equilin. Once increases in estrone or equilin are detected, the resin is taken off-line for elution and regeneration. In the meantime, the effluent flow from the HP2MG column is directed to input into the process of Example 6 above. The HP2MG loaded with estrone, equiline and other materials is eluted with a 2% NaOH in water:methanol (1:1) solution, which is applied until no further desired components are eluted therefrom.

Example 9

Isolation of Crystals-Procedure A

The eluates collected in Examples 6-8 are separately concentrated in a rota-vap under a vacuum pressure of not greater than 10 mm Hg and a temperature not in excess of 40° C. Each eluate is concentrated until reduced to a very viscous dark liquid. The vacuum is removed and acetone is added to each residue. Upon mixing with the acetone there is a color change which indicates completeness of the mixing. Each residue/acetone mixture is then filtered through diatomaceous earth with the filtrates separately collected, and each is stored at 5° C. The remaining residue is discarded.

The collected and stored filtrates are each separately evaporated under vacuum until a heavy black mass remains. Each black mass is separately dissolved in water and sodium chloride is added until saturated, followed by the addition of n-butanol. Each aqueous n-butanol mixture is further thoroughly mixed and allowed to stand in order to separate the aqueous and non-aqueous phases. The lower aqueous phase is discarded from each mixture. The upper n-butanol phases each contain one or more constituents that make up conjugated estrogens are retained for processing. Each n-butanol phase is then evaporated to dryness via a rota-vap, resulting in a dark brown powder, which is hygroscopic. Each hygroscopic dark brown powder is washed with warm toluene, which washes away the free estrogens and peak 39 (that is the a peak appearing at about 39 minutes into the HPLC when the full HPLC run time is about 12 hours—see FIGS. 1-7, which peak appears to be a degredation product from the PMU). The toluene (with the free estrogens) may be recovered for recovery of the steroids contained therein (for use thereof as is, for conversion to sulfate esters thereof, or conversion to other molecules having the steroidal tetracyclic structure); however, in this example, they are discarded.

Each residue resulting from the toluene wash is separately dissolved in warm acetonitrile and the solutions are stored in a refrigerator (approximately 3° C. to 5° C.) for about 48 hours. Each solution is analyzed for its particular steroidal content and then evaporated under reduced pressure to yield light brown crystals, which crystals are labeled. The data on the steroid content of each analyzed solution is kept in a database for use in a reblending process.

Example 10

Alternate Isolation of Crystals—Procedure B

Figure 9:
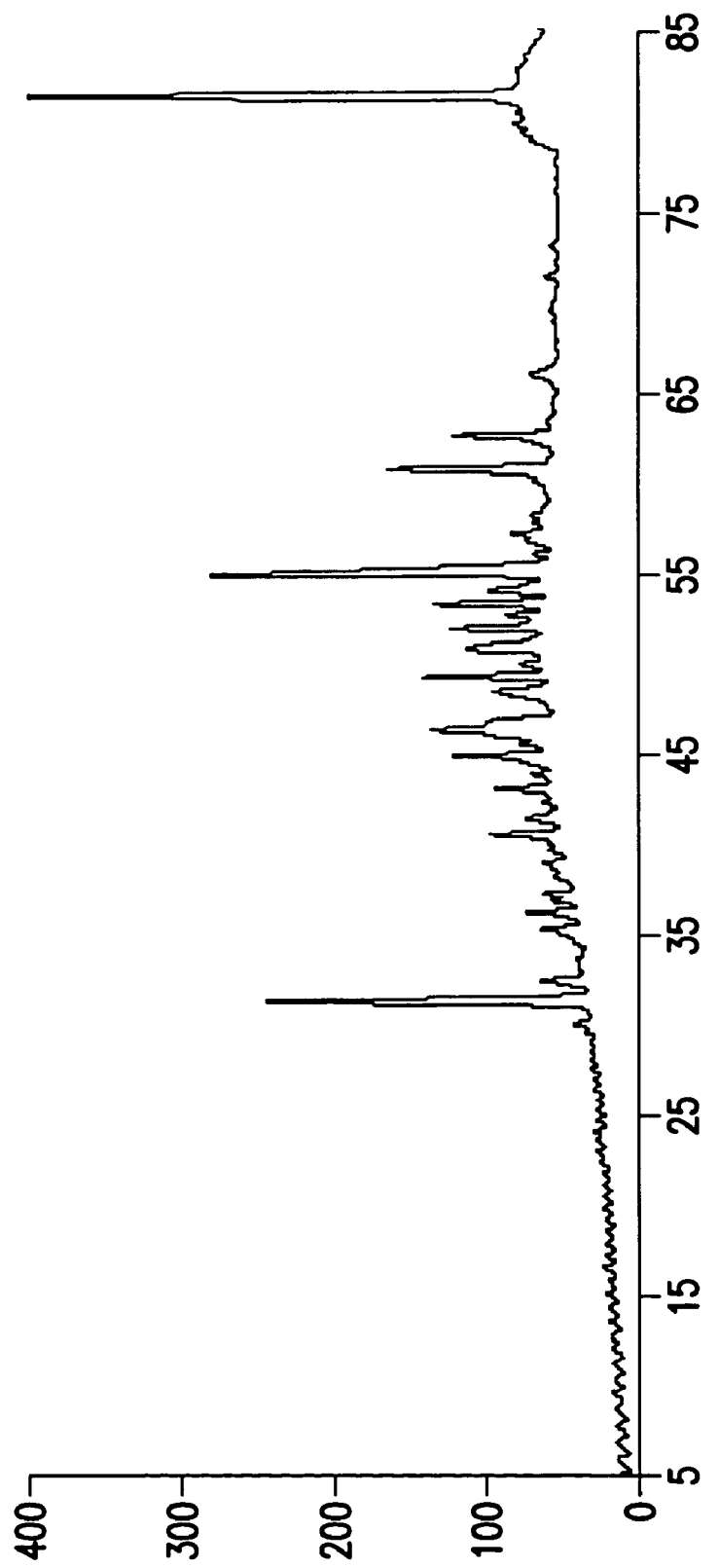
FIG. 9 is an HPLC (during the first 85 minutes) of a single sample of pregnant mare's urine that was processed according to the invention resin extractions, the eluates of the non-ionic resin and the cationic exchange resin combined, which combined solution was dried, the residue washed with methanol and then with toluene, the residue dissolved in n-butanol, and crystallized.

In an alternate purification procedure, the eluates collected in Examples 6-8 are separately concentrated in a rota-vap under a vacuum pressure of not greater than 10 mm Hg and a temperature not in excess of 40° C. Each eluate is concentrated until reduced to a very viscous dark liquid. The vacuum is removed and dry methanol is added to dissolve the material. A solution of the soluble materials and a residue result. To the residue acetone is added and the resulting solution is separated from undissolved materials by filtration. The acetone is then removed from the solution under vacuum evaporation and the resulting residue is washed with toluene and then with n-butanol. The liquid phase is separated from undissolved materials by filtration and the n-butanol is then removed by vacuum evaporation. To give a desired product. An HPLC of a mixed eluate from the non-ionic and cationic exchange columns processed in this manner is shown in FIG. 9.

Example 11

Further Purification Under Alternate Procedure B

Figure 10:
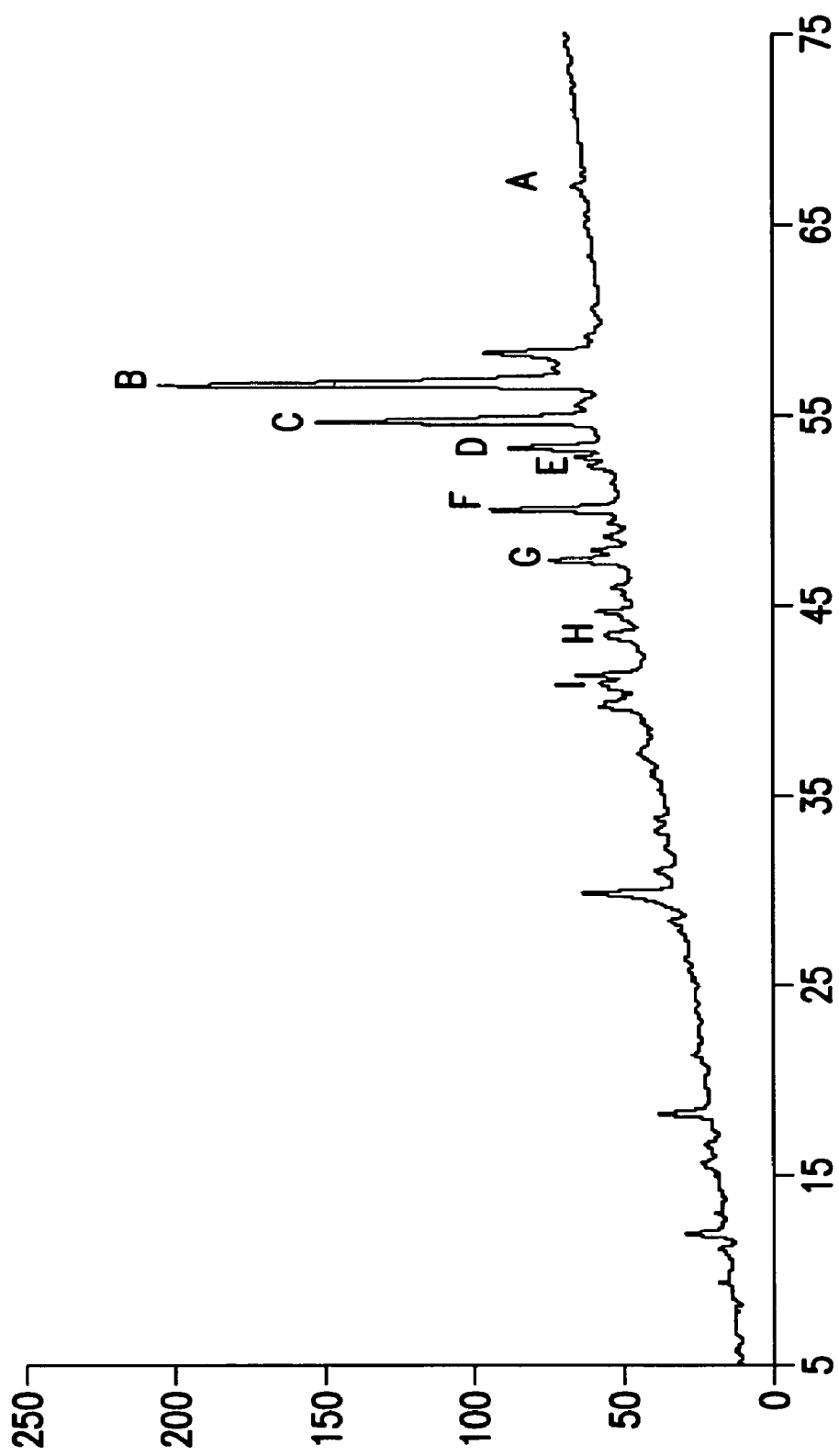
FIG. 10 is an HPLC (during the first 75 minutes) of a sample of the material shown in FIG. 9, but further recrystallized from n-butanol. 9 peaks are identified for comparison with FIG. 11.

The product obtained in Example 10 is further purified by recrystallization in n-butanol. An HPLC of a mixed eluate from the non-ionic and cationic exchange columns processed in this manner is shown in FIG. 10.

Example 12

Reference Product Profile Determination

PREMARIN conjugated estrogens is selected as a reference product for the ultimate preparation of a potential generic equivalent thereto. Multiple samples of a number of different lots of PREMARIN are obtained and analyzed via gas and liquid chromatography in accordance with the FDA Guidance for Industry Conjugated Estrogens, USP-LC, MS Method for Quantitative Characterization and Documentation of Qualitative Pharmaceutical Equivalence, dated March 2000 ("FDA Guidance"). Samples are prepared by crushing PREMARIN Tablets, extracting the crushed tablets with methanol and analyzing the solution. An HPLC of a single lot of PREMARIN tablets is shown in FIG. 11.

Example 13

Non-Limiting HPLC Testing Conditions

In the foregoing Examples, and as used in the procedures generating the Figures, Test samples for HPLC analysis are prepared in the case of powders by adding a sample of powder approximately equal to 0.625 mg of conjugated estrogens to a centrifuge tube. (Crystals and liquid samples are reduced to solids and then processed in the same manner as powdered samples.) 5 ml of water is added and the solution is placed on a vortex mixer (set on full speed) for 5 minutes and then centrifuged at 2500 rpm for 10 minutes. The solution is filtered through a 0.45 micron cellulose nitrate membrane filter into an LC injection vial. A mobile phase A is comprised of 1 ml trifluoroacetic acid and enough water to make 1 liter. A mobile phase B is comprised of 1 ml of trifluoroacetic acid and sufficient acetonitrile to make 1 liter. The initial mobile phase is trifluoroacetic acid and water. The final mobile phase is trifluoroacetic acid in acetonitrile and the rate of change in water to acetonitrile is determined by the time frame in which the HPLC test is intended to be completed. For FIGS. 1-7, this rate of water to acetonitrile change was completed over a period of about 1.5-2 hours, whereas the rate of water to acetonitrile change was completed in about 1 hour (FIG. 8), about 1.5 hours (FIG. 9), and about 1.25 hours (FIGS. 10-11).

We claim:
1. A method for obtaining steroids from urine, said urine containing phenolic constituents, a first group of esterified steroid constituents (first ESC) and a second group of esterified steroid constituents (second ESC), said method comprising:
    a. contacting urine, optionally pretreated by:
        (i) filtering to remove extraneous solid matter, adjusting and/or buffering the pH of the urine to about 8.0 or more; or
        (ii) reducing said phenolic constituents of said urine to result in a reduced-phenolic content urine and a high phenolic content portion; or
        both of (i) and (ii), or
        (iii) contacting the urine, the product of (i), a reduced-phenolic content urine product of (ii), or a product of (i) and (ii), with a first non-ionic resin (first resin) capable of extracting at least a portion of non-steroidal organic materials;
    with a second non-ionic resin (second resin), said second resin capable of extracting at least one constituent of said first ESC without substantially extracting said second ESC, to result in a first ESC constituent laden second resin and a liquid remainder, and separating said first ESC constituent laden second resin from said liquid remainder;
b. contacting said liquid remainder with a third cationic resin (third resin), said third resin capable of extracting at least one constituent of said second ESC from said liquid remainder to result in a second ESC constituent laden third resin and a second liquid remainder and separating said second ESC constituent laden third resin from said second liquid remainder; and
c. independently recovering the first ESC from said first ESC laden second resin and the second ESC from said second ESC laden third resin.

2. The method of claim 1 wherein said urine is the urine of a pregnant mammal.

3. The method of claim 2 wherein said mammal is a mare.

4. The method of claim 1 wherein said urine is filtered to remove extraneous solid matter.

5. The method of claim 1 wherein said pH of said urine is adjusted or buffered to at least 8.0.

6. The method of claim 5 wherein said pH of said urine is adjusted or buffered in the range of about 8.25 to about 12.0.

7. The method of claim 6 wherein said pH of said urine is adjusted or buffered in the range of about 8.5 to about 10.

8. The method of claim 7 wherein said pH of said urine is adjusted or buffered in the range of about 8.5 to about 9.6.

9. The method of claim 1 wherein said pH of said urine is adjusted or buffered with sodium sulfite.

10. The method of claim 1 wherein said first non-ionic resin is selected from the group consisting of polymethacrylates, polyacrylates, and poly(methacrylate/acrylate).

11. The method of claim 10 wherein said first non-ionic resin is a polymethacrylate.

12. The method of claim 1 wherein said second resin is a non-ionic resin selected from the group consisting of polystyrene-divinylbenzenes, polyphenolics, polymethacrylates, polyacrylates, and poly(methacrylate/acrylate).

13. The method of claim 1 wherein said third resin is a weakly cationic exchange resin.

14. The method of claim 13 wherein said third resin is selected from the group consisting of (a) polystyrene-divinylbenzene resins having side groups selected from the group consisting of sulfate groups, carboxy groups, phosphate groups, and mixtures thereof and (b) poly(meth)acrylic acids.

15. The method of claim 14 wherein said third resin is a polystyrene-divinylbenzene resins having sulfate groups.

16. The method of claim 1 wherein the at least one constituent of said first ESC is recovered from said first ESC laden second resin and the at least one constituent of said second ESC is recovered from said second ESC laden third resin independently by elution of each respective laden resin with an elution fluid comprising at least one water-miscible organic solvent.

17. The method of claim 16 wherein said water miscible organic solvent is selected from the group consisting of water-miscible ethers, lower aliphatic alcohols, lower aliphatic ketones, and mixtures thereof.

18. The method of claim 17 wherein said elution fluid is a lower aliphatic alcohol mixture with water.

19. The method of claim 18 wherein said elution fluid is a water-ethanol mixture or a water-isopropanol mixture.

20. The method of claim 16 wherein said elution fluid contains about 2% w/w alkali metal hydroxide.

21. The method of claim 1 wherein during said recovery of said first ESC, recovery is obtained in multiple fractions thereof and during said recovery of said second ESC, recovery is obtained in multiple fractions thereof.

22. The method of claim 21 wherein each of said multiple fractions of said first ESC and said multiple fractions of said second ESC is then processed independently to ascertain the steroid content of each fraction.

23. The method of claim 21 wherein each of said multiple fractions is independently dried to form a dried solid.

24. The method of claim 16 wherein said recovered materials are stored for later recombination so as to arrive at a product having a steroid constituent and concentration profile that matches a pre-determined steroid product profile.

25. The method of claim 21 wherein said multiple fractions are recovered and are stored for later recombination so as to arrive at a product having a steroid constituent and concentration profile that matches a pre-determined steroid product profile.

26. The method of claim 23 wherein said dried solid materials are stored for later recombination so as to arrive at a product having a steroid constituent and concentration profile that matches a pre-determined steroid product profile.

27. A method for obtaining steroids from urine, said urine containing phenolic constituents, a first group of esterified steroid constituents (first ESC) and a second group of esterified steroid constituents (second ESC), said method comprising:
a. contacting urine with a non-ionic resin, said non-ionic resin capable of extracting at least one constituent of said first ESC without substantially extracting said second ESC, to result in a first ESC constituent laden non-ionic resin and a liquid remainder, and separating said first ESC constituent laden non-ionic resin from said liquid remainder;
b. contacting said liquid remainder with a cationic resin, said cationic resin capable of extracting at least one constituent of said second ESC from said liquid remainder to result in a second ESC constituent laden cationic resin and a second liquid remainder, and separating said second ESC constituent laden cationic resin from said second liquid remainder; and
c. independently recovering the first ESC from said first ESC laden non-ionic resin and the second ESC from said second ESC laden cationic resin.

* * * * *